(12) United States Patent
Bennett et al.

(10) Patent No.: US 11,197,936 B2
(45) Date of Patent: Dec. 14, 2021

(54) METHODS AND COMPOSITIONS FOR TREATMENT OF DISORDERS AND DISEASES INVOLVING RDH12

(71) Applicant: The Trustees of the University of Pennsylvania, Philadelphia, PA (US)

(72) Inventors: Jean Bennett, Bryn Mawr, PA (US); Junwei Sun, Philadelphia, PA (US); Vidyullatha Vasireddy, Wayne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 54 days.

(21) Appl. No.: 16/314,179

(22) PCT Filed: Jul. 7, 2017

(86) PCT No.: PCT/US2017/041122
§ 371 (c)(1),
(2) Date: Dec. 28, 2018

(87) PCT Pub. No.: WO2018/009814
PCT Pub. Date: Jan. 11, 2018

(65) Prior Publication Data
US 2019/0151473 A1    May 23, 2019

Related U.S. Application Data

(60) Provisional application No. 62/359,777, filed on Jul. 8, 2016.

(51) Int. Cl.
```
A61K 48/00      (2006.01)
A61P 27/02      (2006.01)
A61K 9/00       (2006.01)
C12Q 1/68       (2018.01)
C12N 15/63      (2006.01)
C12N 15/67      (2006.01)
```

(52) U.S. Cl.
CPC ........ *A61K 48/0058* (2013.01); *A61K 9/0019* (2013.01); *A61K 9/0048* (2013.01); *A61K 48/005* (2013.01); *A61K 48/0008* (2013.01); *A61K 48/0091* (2013.01); *A61P 27/02* (2018.01); *C12N 15/63* (2013.01); *C12N 15/67* (2013.01); *C12Q 1/68* (2013.01); *C12N 2750/14143* (2013.01); *C12N 2800/22* (2013.01)

(58) Field of Classification Search
CPC ... A61P 27/02; A61K 9/0048; A61K 48/0091; C12N 2750/14143; C12N 2800/22; C12N 15/86; C12Y 101/01105
See application file for complete search history.

(56) References Cited

U.S. PATENT DOCUMENTS

| | | |
|---|---|---|
| 5,139,941 A | 8/1992 | Muzyczka et al. |
| 5,478,745 A | 12/1995 | Samulski et al. |
| 5,741,683 A | 4/1998 | Zhou et al. |
| 6,057,152 A | 5/2000 | Samulski et al. |
| 6,204,059 B1 | 3/2001 | Samulski et al. |
| 6,268,213 B1 | 7/2001 | Samulski et al. |
| 6,491,907 B1 | 12/2002 | Rabinowitz et al. |
| 6,596,535 B1 | 7/2003 | Carter |
| 6,660,514 B1 | 12/2003 | Zolotukhin et al. |
| 6,951,753 B2 | 10/2005 | Shenk et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao |
| 7,439,065 B2 | 10/2008 | Ferrari et al. |
| 7,456,683 B2 | 11/2008 | Takano et al. |
| 7,561,972 B1 | 7/2009 | Welch |
| 7,561,973 B1 | 7/2009 | Welch |
| 7,588,772 B2 | 9/2009 | Kay et al. |
| 7,629,322 B2 | 12/2009 | Kleinschmidt |
| 7,790,449 B2 | 9/2010 | Gao |
| 7,888,112 B2 | 2/2011 | Hermanson et al. |

(Continued)

FOREIGN PATENT DOCUMENTS

| | | |
|---|---|---|
| EP | 1310571 | 2/2006 |
| WO | 1999/15685 | 4/1999 |

(Continued)

OTHER PUBLICATIONS

Kroptova et al. (Molecular Biology, 47(2): 280-292, 2012 (Year: 2012).*

(Continued)

*Primary Examiner* — Richard A Schnizer
(74) *Attorney, Agent, or Firm* — Howson & Howson LLP

(57) ABSTRACT

Codon optimized nucleic acid sequences for RDH12 are provided, as well as recombinant viral vectors, such as AAV, expression cassettes, proviral plasmids or other plasmids containing the codon optimized sequence for functional RDH12. Recombinant vectors are provided that express the codon optimized, functional RDH12. Compositions containing these codon optimized sequences are useful in methods for treating, retarding or halting certain blinding diseases resulting from the absence, deficiency or inappropriate expression of RDH12. Other compositions and methods are providing for correcting a non-functional, defective or inadequately expressed native RDH12.

17 Claims, 15 Drawing Sheets

Specification includes a Sequence Listing.

(56) References Cited

U.S. PATENT DOCUMENTS

| | | | |
|---|---|---|---|
| 7,906,111 | B2 | 3/2011 | Wilson et al. |
| 8,147,823 | B2 | 4/2012 | Acland et al. |
| 9,249,425 | B2 | 2/2016 | Bennett |
| 10,392,622 | B2 * | 8/2019 | Lewis ............... C12N 15/63 |
| 2007/0036760 | A1 | 2/2007 | Wilson et al. |
| 2009/0199733 | A1 | 8/2009 | Vendenberghe et al. |
| 2014/0010861 | A1 | 1/2014 | Bancel et al. |
| 2015/0259395 | A1 * | 9/2015 | Chalberg ............ C12N 15/86 514/44 R |
| 2016/0015288 | A1 | 1/2016 | Neitz et al. |

FOREIGN PATENT DOCUMENTS

| | | |
|---|---|---|
| WO | 2003/042397 | 5/2003 |
| WO | 2005/033321 | 5/2005 |
| WO | 2006/110689 | 10/2006 |
| WO | 2011/126808 | 10/2011 |
| WO | 2012/158757 | 11/2012 |
| WO | 2013/049493 A1 | 4/2013 |
| WO | 2014/011210 | 1/2014 |
| WO | 2015012924 A2 | 1/2015 |
| WO | WO 2015/075154 | 5/2015 |
| WO | 2016019364 A1 | 2/2016 |
| WO | 2018009814 A1 | 1/2018 |

OTHER PUBLICATIONS

Qiao et al. (Biomed. Res. Int. 2020: 4252580, 13 pages, 2020) (Year: 2020).*
Fingert et al. (Arch Ophthalmol. 2008;126(9):1301-1307) (Year: 2008).*
Sarkar et al. (Frontiers in Genetics 11: article 335, Apr. 2020) (Year: 2020).*
Kasus-Jacobi et al. (Mechanisms of RDH12-Induced Leber Congenital Amaurosis and Therapeutic Approaches, In Advances in Ophthalmology, Dr Shimon Rumelt (Ed.), pp. 473-496, 2012) (Year: 2012).*
Sarkar et al. (Experimental Eye Research 188 (2019) 107793, 6 pages) (Year: 2019).*
Sofia et al. (TVST 9(8): article 30, 7 pages, Jul. 17, 2020) (Year: 2020).*
Tuohy ("A report on a workshop for accelerating the development of treatments for inherited retinal degenerations (IRDs)",Sep. 2020, retrieved from http://brief.euretina.org/research/a-report-on-a-workshop-for-accelerating-the-development-of-treatments-for-inherited-retinal-degenerations-irds) (Year: 2020).*
Rowe-Rendleman (Invest Ophthalmol Vis Sci. 2014;55:2714-2730) (Year: 2014).*
Kim (TVST 3(5): article 7, 10 pages, 2014) (Year: 2014).*
International Search Report dated Oct. 2, 2017 in corresponding International Patent Application PCT/US17/41122, filed Jul. 7, 2017.
Written Opinion dated Oct. 2, 2017 in corresponding International Patent Application PCT/US17/41122, filed Jul. 7, 2017.
Beltran et al, rAAV2/5 gene-targeting to rods: dose-dependent efficiency and complications associated with different promotersGene Therapy, Sep. 2010, 17(9):1162-74.
Buie et el., "Self-complementary AAV Virus (scAAV) Safe and Long-term Gene Transfer in the Trabecular Meshwork of Living Rats and Monkeys", Invest Ophthalmol Vis Sci., vol. 51(1):236-248, Jan. 2010.
Buning et al., 2008, "Recent developments in adeno-associated virus vector technology," J. Gene Med. 10:717-733.
Cai, X et al, A 350 bp region of the proximal promoter of Rds drives cell-type specific gene expression., Exp Eye Res. Aug. 2010: 91(2):186-194.
Cong, L., et al. Multiplex genome engineering using CRISPR/Cas systems. Science. Feb. 15, 2013;339(6121):819-23. doi: 10.1126/science.1231143. (Epub Jan. 3, 2013).

Dalkara et al, In Vivo-Directed Evolution of a New Adeno-Associated Virus for Therapeutic Outer Retinal Gene Delivery from the Vitreous, Sci Transl Med 5, 189ra76 (Jun. 2013).
Damdindorj et al., (Aug. 2014) A Comparative Analysis of Constitutive Promoters Located in Adeno-Associated Viral Vectors. PLoS ONE 9(8): e106472.
Diehl, K-H et al, A Good Practice Guide to the Administration of Substances and Removal of Blood, Including Routes and Volumes. J. Applied Toxicology, 21:15-23 (Sep. 2001).
Fisher et al., Transduction with recombinant adeno-associated virus for gene therapy is limited by leading-strand synthesis, Journal of Virology, vol. 70(1):520-532, Jan. 1996.
Grieger, MC & Samulski, RJ, 2005, "Adeno-associated virus as a gene therapy vector: Vector development, production and clinical applications," Adv. Biochem. Engin/Biotechnol. 99: 119-145.
Kachi et al., "Equine Infectious Anemia Viral Vector-Mediated Codelivery of Endostatin and Angiostatin Driven by Retinal Pigmented Epithelium-Specific VMD2 Promoter Inhibits Choroidal Neovascularization", Human Gene Therapy, vol. 20:31-9, Jan. 2009.
Kay et al, Apr. 2013, Targeting Photoreceptors via Intravitreal Delivery Using Novel, Capsid-Mutated AAV Vectors, PLoS One. 2013; 8(4): e62097.
Kozak et al., "An analysis of 5'-noncoding sequences from 699 vertebrate messenger RNAs", Nucleic Acids Res., vol. 15(20): 8125-8148, Oct. 1987.
Ku et al, Dec. 2011, Gene therapy using self-complementary Y733F capsid mutant AAV2/8 restores vision in a model of early onset Leber congenital amaurosis, Hum Mol Genet., 20(23): 4569-4581.
Lambard et al., "Expression of Rod-Derived Cone Viability Factor: Dual Role of CRX in Regulating Promoter Activity and Cell-Type Specificity", PLoS One, vol. 5(10):e13025, Oct. 2010.
Lock M, et al, Absolute determination of single-stranded and self-complementary adeno-associated viral vector genome titers by droplet digital PCR. Hum Gene Ther Methods. Apr. 2014;25(2):115-25. doi: 10.1089/hgtb.2013.131. (Epub Feb. 14, 2014).
Mali, P, et al. RNA-guided human genome engineering via Cas9. Science. Feb. 15, 2013;339(6121):823-6, doi: 10.1126/science.1232033. (Epub Jan. 3, 2013).
McCarty, DM et al., "Self-complementary recombinant adeno-associated virus (scAAV) vectors promote efficient transduction independently of DNA synthesis", Gene Therapy, (Aug. 2001), vol. 8, No. 16, pp. 1248-1254.
McLaughlin et al., "Adeno-Associated Virus General Transduction Vectors: Analysis of Proviral Structures", J. Virol., vol. 62:1963, Jun. 1988.
Meindl et al., "A gene (RPGR) with homology to the RCC1 guanine nucleotide exchange factor is mutated in X-linked retinitis pigmentosa (RP3)", Nat Genet, vol. 13:35-42, May 1996.
Morrissey et al., "PRE-1, a cis element sufficient to enhance cone-and-rod-specific expression in differentiating zebrafish photoreceptors", BMC Dev, Biol, vol. 11:3, Jan. 2011.
Mowat et al., "Tyrosine capsid-mutant AAV vectors for gene delivery to the canine retina from a subretinal or intravitreal approach", Gene Therapy, vol. 21:96-105, Jan. 2014.
Mussolino et al., "AAV-mediated photoreceptor transduction of the pig cone-enriched retina", Gene Ther, vol. 18(7):637-45, Jul. 2011.
Nicoud et al., "Development of photoreceptor-specific promoters and their utility to investigate EIAV lentiviral vector mediated gene transfer to photoreceptors", J. Gene Med, vol. 9(12):1015-23, Dec. 2007.
Ran FA, et al., Genome engineering using the CRISPR-Cas9 system. Nat Protoc. Nov. 2013;8(11):2281-2308. doi: 10.1038/nprot.2013.143. (Epub Oct. 24, 2013).
Ryals et al., "Quantifying transduction efficiencies of unmodified and tyrosine capsid mutant AAV vectors in vitro using two ocular cell lines", Mol Vis. vol. 17:1090-102, Apr. 2011.
Shalem, O et al., Genome-Scale CRISPR-Cas9 Knockout Screening in Human Cells. Science, Jan. 2014, 343(6166):84-87.
Shu, X et al., Functional Characterization of the Human RPGR Proximal Promoter., Invest. Ophthalmol. Vis. Sci., May 2012; 53:3951-3958.

(56) References Cited

OTHER PUBLICATIONS

Thompson, DA et al, Nov. 2005, Retinal degeneration associated with RDH12 mutations results from decreased 11-cis retinal synthesis due to disruption of the visual cycle. Human Mol. Genet., 14(24):3865-3875.
Thompson et al., "A comprehensive comparison of multiple sequence alignments", Nucl. Acids. Res., vol. 27(13):2682-2690, Jul. 1999.
Vervoort et al., "Mutational hot spot within a new RPGR exon in X-linked retinitis pigmentosa", Nat Genet, vol. 25(4):462-466, Aug. 2000.
Vervoort et al., "Mutations of RPGR in X-linked Retinitis Pigmentosa (RP3)", Human Mutation, vol. 19:486-500, Apr. 2002.
Wang et al., "Sustained correction of bleeding disorder in hemophilia B mice by gene therapy", Proc. Natl. Acad. Sci., USA, vol. 96(7):3906-3910, Mar. 1999.
Yin H, et al. Genome editing with Cas9 in adult mice corrects a disease mutation and phenotype. Nat Biotechnol. Jun. 2014;32(6):551-3. doi: 10.1038/nbt.2884. (Epub Mar. 30, 2014).
Zhang H, et al., Adenovirus-adeno-associated virus hybrid for large-scale recombinant adeno-associated virus production. Hum Gene Ther. Sep. 2009;20(9):922-9. doi: 10.1089/hum.2009.125. (Online Ahead of Editing: Jul. 20, 2009).
Albakri, A et al., Elevation Deficiency in Children with Recessive RDH12-Related Retinopathy. Journal of AAPOS. Dec. 2015; vol. 19, No. 6; pp. 568-570.
Hamilton, MM et at., Repeated Administration of Adenovector in the Eye Results in Efficient Gene Delivery. Investigative Ophthalmology and Visual Sciences. Jan. 2006; vol. 47, No. 1; pp. 299-305.
Lee, SA et al., Overproduction of Bioactive Retinoic Acid in Celts Expressing Disease-associated Mutants of Retinol Dehydrogenase 12. Journal of Biological Chemistry. Oct. 9, 2009; vol. 282, No. 49; pp. 35621-35628.
Mackay, DS et al., RDH12 Retinopathy: Novel Mutations and Phenotypic Description. Molecular Vision. Oct. 19, 2011; vol. 17; pp. 2706-2716.
Extended European Search Report issued in European Patent Application No. 17824989.2, dated Nov. 27, 2019.
Thompson et al., AAV-mediated Expression of Human Rdh12 in Mouse Retina, ARVO Annual Meeting Abstract, Investigative Ophthalmology & Visual Science, vol. 53(1916), Mar. 2012.
Office Action issued in corresponding Japanese Patent Application No. 2019-500531, dated Jun. 9, 2021, with translation provided by local agent.

* cited by examiner

FIG. 1A

SEQ ID NO: 5 over SEQ ID NO: 1

```
ATGTTGGTCACCCTCGGACTCCTTACCTCATTTTTCTCCTTCCTGTACATGGTCGCCCCG  72
||| |||||||||| ||||||| || ||||| ||||| |||||||||| ||||| || ||
ATGCTGGTCACCTTGGGACTGCTCACCTCCTTCTTCTCGTTCCTGTATATGGTAGCTCCA  60

AGCATTAGAAAGTTCTTCGCCGGCGGAGTGTGTAGGACTAACGTGCAGTTGCCCGGGAAG
||| || |||||||| || || |||||||||| || || |||||| | || || |||
TCCATCAGGAAGTTCTTTGCTGGTGGAGTGTGTAGAACAAATGTGCAGCTTCCTGGCAAG  120

GTCGTGGTGATTACTGGCGCCAACACTGGTATCGGAAAGGAAACTGCGCGGGAACTGGCG
|| |||||||| |||||||||||||| || || || ||||| || || | || || ||
GTAGTGGTGATCACTGGCGCCAACACGGGCATTGGCAAGGAGACGGCCAGAGAGCTCGCT  180

TCCAGAGGTGCCCGCGTGTACATTGCATGCCGCGACGTGCTGAAGGGAGAATCCGCCGCG
| |||| ||||| || || |||| ||| | || | |||||||| || || || ||
AGCCGAGGAGCCCGAGTCTATATTGCCTGCAGAGATGTACTGAAGGGGGAGTCTGCTGCC  240

TCCGAGATCCGGGTGGACACCAAAAATAGCCAGGTGCTCGTGCGGAAGCTGGATCTGTCC
|| |||||| ||||| || || ||  ||||||||| |||||||  |||| || |||
AGTGAAATCCGAGTGGATACAAAGAACTCCCAGGTGCTGGTGCGGAAATTGGACCTATCC  300

GACACCAAGTCAATCAGGGCCTTTGCCGAGGGGTTCCTGGCTGAAGAGAAGCAGCTCCAC
|||||||| || ||| | ||||||||  ||||| || || |||| || ||||||||||
GACACCAAATCTATCCGAGCCTTTGCTGAGGGCTTTCTGGCAGAGGAAAAGCAGCTCCAT  360

ATTCTGATCAACAACGCCGGGGTCATGATGTGCCCCTACTCAAAGACCGCAGACGGCTTC
||||||||||||||| || || || ||||||||| || || || || || |||| |||||
ATTCTGATCAACAATGCGGGAGTAATGATGTGTCCATATTCCAAGACAGCTGATGGCTTT  420

GAAACCCACCTGGGCGTGAACCATCTGGGACACTTCCTGCTGACCTATCTGCTGCTGGAG
||||||||||||||| |||||| ||||| ||||||||||  || ||||| ||||| |||||
GAAACCCACCTGGGAGTCAACCACCTGGGCCACTTCCTCCTCACCTACCTGCTCCTGGAG  480
```

FIG. 1B

```
CGACTGAAAGTGTCGGCTCCTGCTCGGGTCGTGAACGTGTCCAGCGTGGCCCATCACATC
|| || || |||||| || ||||| ||||| || || ||||||   ||||| || |||||
CGGCTAAAGGTGTCTGCCCCTGCACGGGTGGTTAATGTGTCCTCGGTGGCTCACCACATT 540

GGAAAGATCCCATTCCACGATCTCCAATCCGAGAAGCGGTACAGCAGGGGCTTCGCGTAC
|| |||||| || ||||||||| |||||    ||||||||| |||||||||||| || ||
GGCAAGATTCCCTTCCACGACCTCCAGAGCGAGAAGCGCTACAGCAGGGGTTTTGCCTAT 600

TGTCACTCGAAGTTGGCCAACGTGCTCTTTACCCGCGAACTGGCCAAGCGGCTGCAGGGC
|| |||   ||| |||||||||||||| ||||| ||| || || |||||||||| || |||
TGCCACAGCAAGCTGGCCAATGTGCTTTTTACTCGTGAGCTGGCCAAGAGGCTCCAAGGC 660

ACTGGCGTGACCACTTACGCCGTGCACCCTGGTGTCGTGCGGTCCGAGCTGGTCCGCCAT
|| || || |||||| ||||| ||||||||| || ||||| || || |||||||||| ||
ACCGGGGTCACCACCTACGCAGTGCACCCAGGCGTCGTCCGCTCTGAGCTGGTCCGGCAC 720

TCCTCTCTTCTGTGCCTCCTGTGGAGACTCTTCTCCCCGTTCGTCAAGACCGCAAGGGAA
||||| || || ||||| || ||| | |||||||||| || |||||||| ||| ||||
TCCTCCCTGCTCTGCCTGCTCTGGCGGCTCTTCTCCCCCTTTGTCAAGACGGCACGGGAG 780

GGAGCCCAAACGAGCCTTCACTGTGCCCTGGCGGAAGGACTGGAGCCGCTTAGCGGAAAG
|| || || || |||||| ||||| ||||||| || || ||||||||| || || || |||
GGGGCGCAGACCAGCCTGCACTGCGCCCTGGCTGAGGGCCTGGAGCCCCTGAGTGGCAAG 840

TACTTCTCGGACTGCAAGCGCACCTGGGTGTCGCCTAGAGCTCGGAACAACAAGACTGCC
||||||    ||||||||||| | |||||||||||| || || || |||||| || ||
TACTTCAGTGACTGCAAGAGGACCTGGGTGTCTCCAAGGGCCCGAAATAACAAAACAGCT 900

GAACGCCTCTGGAATGTGTCCTGCGAGCTGCTGGGAATCAGATGGGAGT    961
|| |||||| ||||||||| ||| ||||| || |||||| | ||||||||
GAGCGCCTATGGAATGTCAGCTGTGAGCTTCTAGGAATCCGGTGGGAGT    949
```

EXPRESSION OF RDH12 PLASMID

FIG. 6A
FIG. 6B
FIG. 6C
FIG. 6D
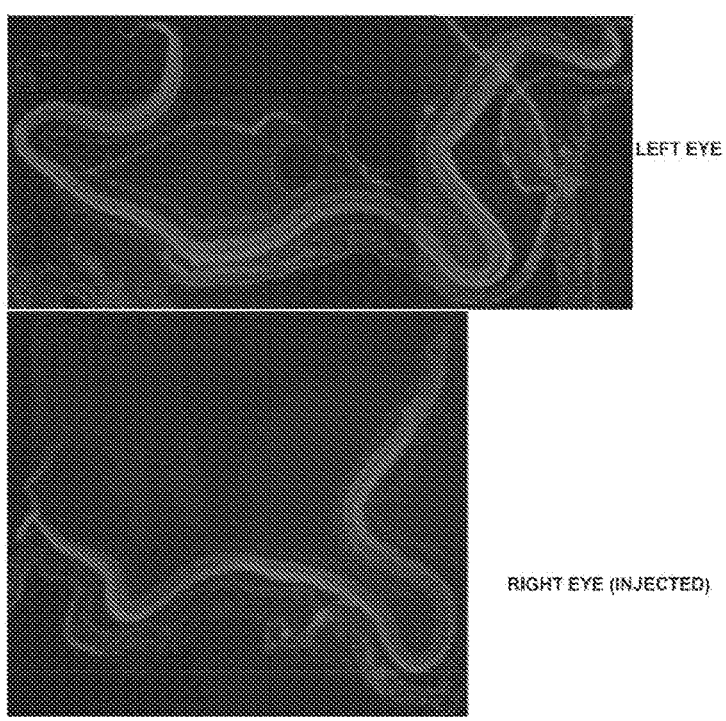
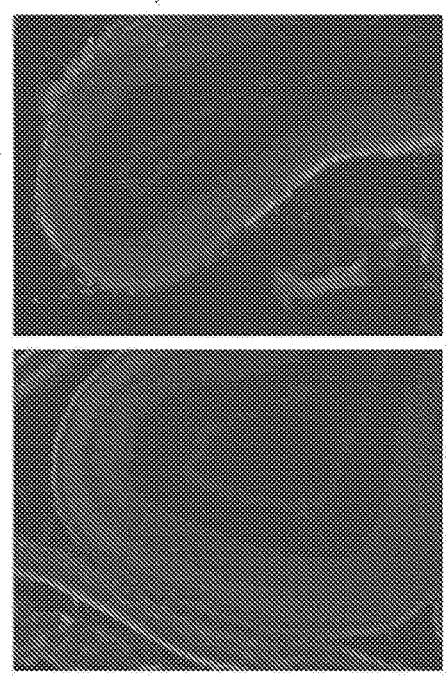

LEFT EYE (UNINJECTED)    Animal 134

Thin ONL

RIGHT EYE (INJECTED WITH AAV8-RDH12-Myc)

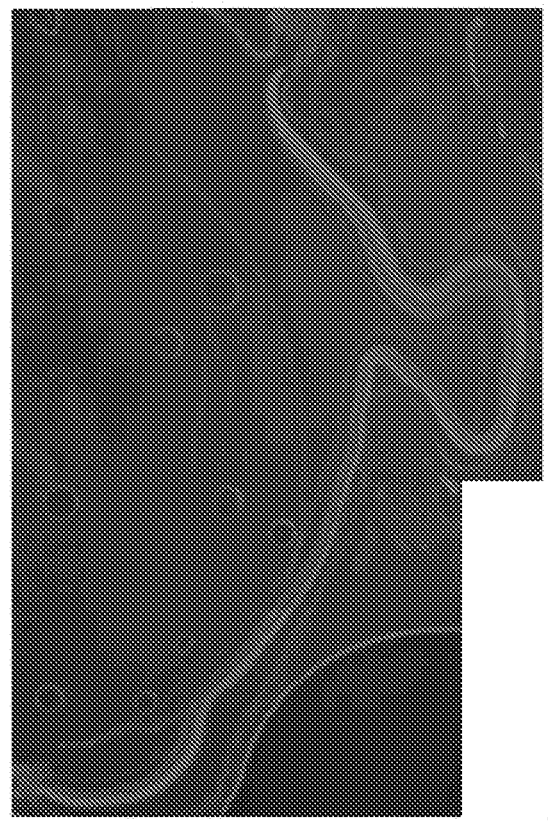
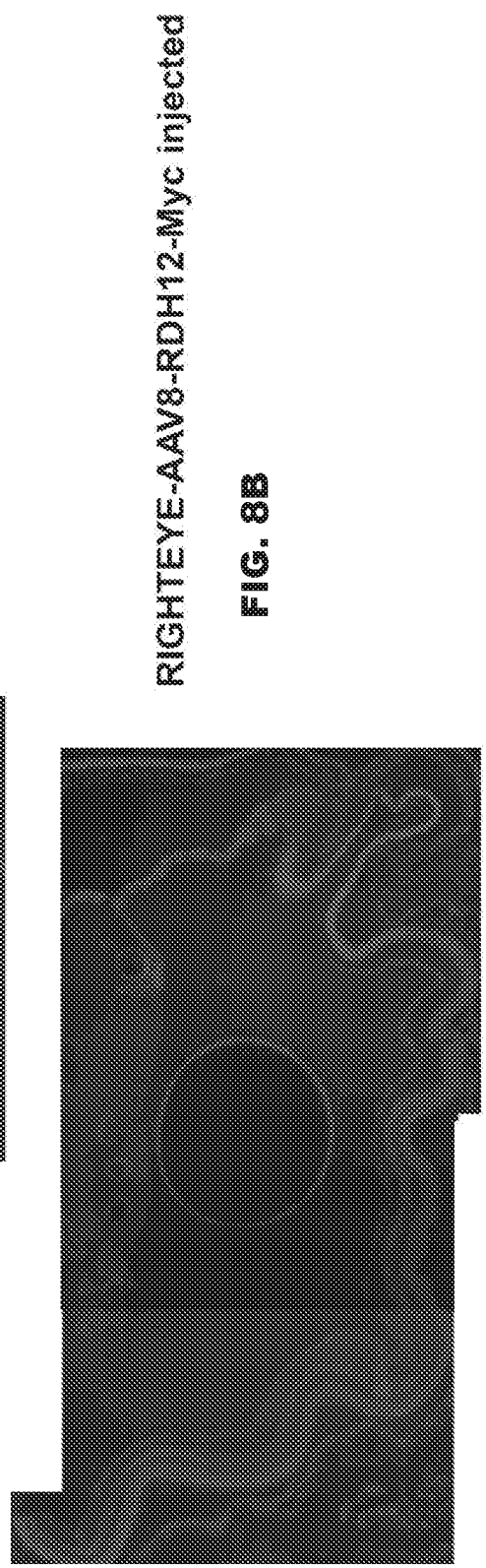
Animal 147
LEFT EYE -UNINJECTED
FIG. 8A
RIGHT EYE-AAV8-RDH12-Myc injected
FIG. 8B

FIG. 9A    LEFT EYE- Uninjected
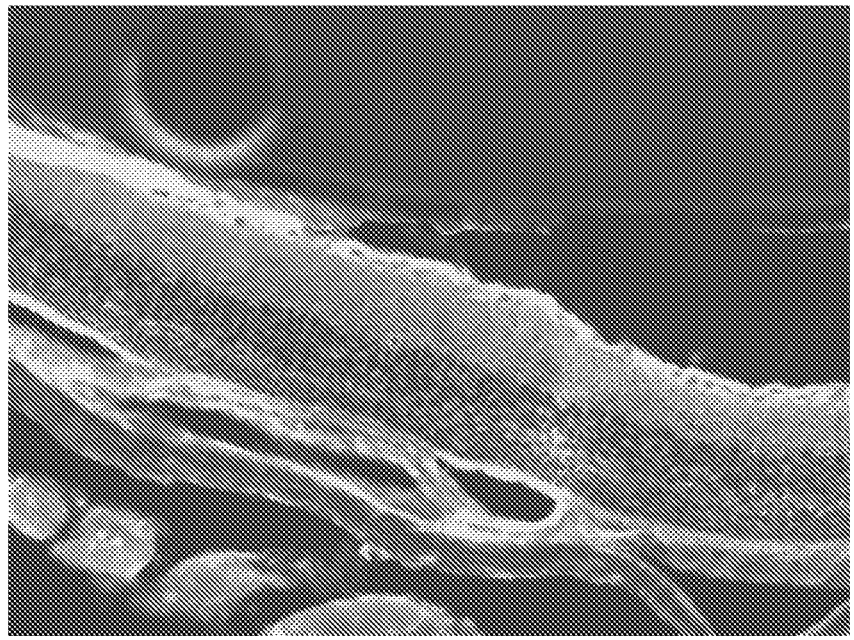
FIG. 9B    RIGHT EYE- Injected
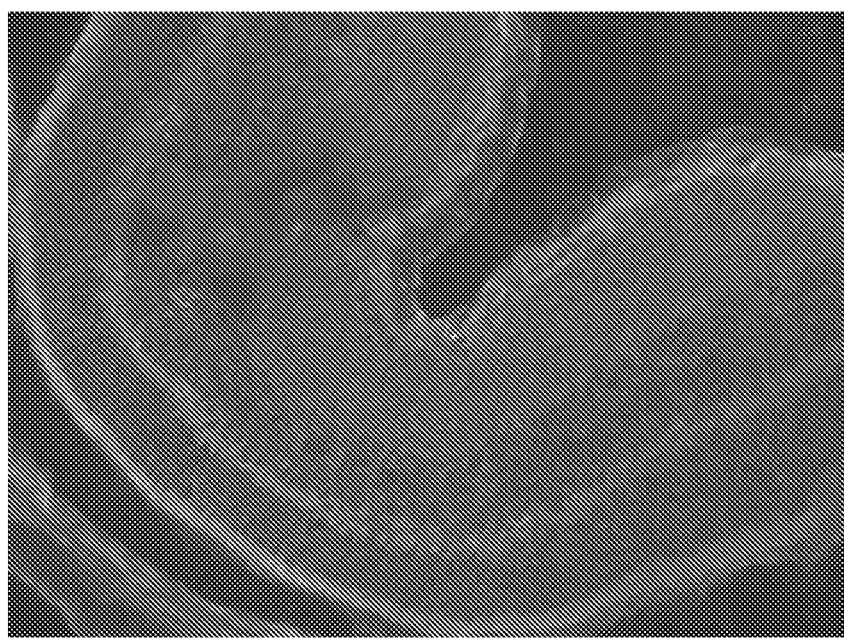

AAV.CBAe.h-Native-RDH12-Myc

SEQUENCE LISTING

```
<160> NUMBER OF SEQ ID NOS: 5

<210> SEQ ID NO 1
<211> LENGTH: 949
<212> TYPE: DNA
<213> ORGANISM: Homo sapiens

<400> SEQUENCE: 1
atgctggtca ccttgggact gctcacctcc ttcttctcgt tcctgtatat ggtagctcca      60
tccatcagga agttctttgc tggtggagtg tgtagaacaa atgtgcagct tcctggcaag     120
gtagtggtga tcactggcgc caacacgggc attggcaagg agacggccag agagctcgct     180
agccgaggag cccgagtcta tattgcctgc agagatgtac tgaaggggga gtctgctgcc     240
agtgaaatcc gagtggatac aaagaactcc caggtgctgg tgcggaaatt ggacctatcc     300
gacaccaaat ctatccgagc ctttgctgag ggctttctgg cagagaaaa gcagctccat      360 attctgatca acaatgcggg agtaatgatg tgtccatatt ccaagacagc tgatggcttt     420
```

-continued

```
gaaacccacc tgggagtcaa ccacctgggc cacttcctcc tcacctacct gctcctggag    480
cggctaaagg tgtctgcccc tgcacgggtg gttaatgtgt cctcggtggc tcaccacatt    540
ggcaagattc ccttccacga cctccagagc gagaagcgct acagcagggg ttttgcctat    600
tgccacagca agctggccaa tgtgcttttt actcgtgagc tggccaagag gctccaaggc    660
accggggtca ccacctacgc agtgcaccca ggcgtcgtcc gctctgagct ggtccggcac    720 tcctcccctgc tctgcctgct ctggcggctc ttctcccct tgtcaagac ggcacgggag     780 ggggcgcaga ccagcctgca ctgcgccctg gctgagggc tggagcccct gagtggcaag     840
tacttcagtg actgcaagag gacctgggtg tctccaaggg cccgaaataa caaaacagct    900
gagcgcctat ggaatgtcag ctgtgagctt ctaggaatcc ggtgggagt                949
```

<210> SEQ ID NO 2
<211> LENGTH: 316
<212> TYPE: PRT
<213> ORGANISM: Homo sapiens

<400> SEQUENCE: 2

```
Met Leu Val Thr Leu Gly Leu Leu Thr Ser Phe Phe Ser Phe Leu Tyr
1               5                   10                  15

Met Val Ala Pro Ser Ile Arg Lys Phe Phe Ala Gly Gly Val Cys Arg
            20                  25                  30

Thr Asn Val Gln Leu Pro Gly Lys Val Val Ile Thr Gly Ala Asn
        35                  40                  45

Thr Gly Ile Gly Lys Glu Thr Ala Arg Glu Leu Ala Ser Arg Gly Ala
    50                  55                  60

Arg Val Tyr Ile Ala Cys Arg Asp Val Leu Lys Gly Glu Ser Ala Ala
65                  70                  75                  80

Ser Glu Ile Arg Val Asp Thr Lys Asn Ser Gln Val Leu Val Arg Lys
                85                  90                  95

Leu Asp Leu Ser Asp Thr Lys Ser Ile Arg Ala Phe Ala Glu Gly Phe
            100                 105                 110

Leu Ala Glu Glu Lys Gln Leu His Ile Leu Ile Asn Asn Ala Gly Val
        115                 120                 125

Met Met Cys Pro Tyr Ser Lys Thr Ala Asp Gly Phe Glu Thr His Leu
    130                 135                 140

Gly Val Asn His Leu Gly His Phe Leu Leu Thr Tyr Leu Leu Leu Glu
145                 150                 155                 160

Arg Leu Lys Val Ser Ala Pro Ala Arg Val Val Asn Val Ser Ser Val
                165                 170                 175

Ala His His Ile Gly Lys Ile Pro Phe His Asp Leu Gln Ser Glu Lys
            180                 185                 190

Arg Tyr Ser Arg Gly Phe Ala Tyr Cys His Ser Lys Leu Ala Asn Val
        195                 200                 205

Leu Phe Thr Arg Glu Leu Ala Lys Arg Leu Gln Gly Thr Gly Val Thr
    210                 215                 220

Thr Tyr Ala Val His Pro Gly Val Val Arg Ser Glu Leu Val Arg His
225                 230                 235                 240

Ser Ser Leu Leu Cys Leu Leu Trp Arg Leu Phe Ser Pro Phe Val Lys
                245                 250                 255

Thr Ala Arg Glu Gly Ala Gln Thr Ser Leu His Cys Ala Leu Ala Glu
            260                 265                 270

Gly Leu Glu Pro Leu Ser Gly Lys Tyr Phe Ser Asp Cys Lys Arg Thr
        275                 280                 285
```

Trp Val Ser Pro Arg Ala Arg Asn Asn Lys Thr Ala Glu Arg Leu Trp
            290                 295                 300

Asn Val Ser Cys Glu Leu Leu Gly Ile Arg Trp Glu
305                 310                 315

<210> SEQ ID NO 3
<211> LENGTH: 977
<212> TYPE: DNA
<213> ORGANISM: Artificial Sequence
<220> FEATURE:
<223> OTHER INFORMATION: Codon-optimized RDH12 DNA sequence

<400> SEQUENCE: 3
gcggccgcca ccatgttggt caccctcgga ctccttacct cattttctc cttcctgtac      60
atggtcgccc cgagcattag aaagttcttc gccggcggag tgtgtaggac taacgtgcag     120
ttgcccggga aggtcgtggt gattactggc gccaacactg gtatcggaaa ggaaactgcg     180
cgggaactgg cgtccagagg tgcccgcgtg tacattgcat gccgcgacgt gctgaaggga     240
gaatccgccg cgtccgagat ccgggtggac accaaaaata gccaggtgct cgtgcggaag     300
ctggatctgt ccgacaccaa gtcaatcagg gcctttgccg aggggttcct ggctgaagag     360
aagcagctcc acattctgat caacaacgcc ggggtcatga tgtgccccta ctcaaagacc     420
gcagacggct cgaaaccca cctgggcgtg aaccatctgg acacttcct gctgacctat      480
ctgctgctgg agcgactgaa agtgtcggct cctgctcggg tcgtgaacgt gtccagcgtg     540
gcccatcaca tcggaaagat cccattccac gatctccaat ccgagaagcg gtacagcagg     600
ggcttcgcgt actgtcactc gaagttggcc aacgtgctct ttacccgcga actggccaag     660
cggctgcagg gcactggcgt gaccacttac gccgtgcacc tggtgtcgt gcggtccgag      720
ctggtccgcc attcctctct tctgtgcctc ctgtggagac tcttctcccc gttcgtcaag     780
accgcaaggg aaggagccca aacgagcctt cactgtgccc tggcgaagg actggagccg      840
cttagcggaa agtacttctc ggactgcaag cgcacctggg tgtcgcctag agctcggaac     900
aacaagactg ccgaacgcct ctggaatgtg tcctgcgagc tgctgggaat cagatgggag     960
tgatgatcat gagatct                                                   977

<210> SEQ ID NO 4
<211> LENGTH: 320
<212> TYPE: PRT
<213> ORGANISM: Artificial Sequence
<220> FEATURE:
<223> OTHER INFORMATION: Translated functional RDH12 protein sequence.

<400> SEQUENCE: 4

Ala Ala Ala Thr Met Leu Val Thr Leu Gly Leu Leu Thr Ser Phe Phe
1               5                   10                  15

Ser Phe Leu Tyr Met Val Ala Pro Ser Ile Arg Lys Phe Phe Ala Gly
            20                  25                  30

Gly Val Cys Arg Thr Asn Val Gln Leu Pro Gly Lys Val Val Ile
            35                  40                  45

Thr Gly Ala Asn Thr Gly Ile Gly Lys Glu Thr Ala Arg Glu Leu Ala
50                  55                  60

Ser Arg Gly Ala Arg Val Tyr Ile Ala Cys Arg Asp Val Leu Lys Gly
65                  70                  75                  80

Glu Ser Ala Ala Ser Glu Ile Arg Val Asp Thr Lys Asn Ser Gln Val
                85                  90                  95

Leu Val Arg Lys Leu Asp Leu Ser Asp Thr Lys Ser Ile Arg Ala Phe
            100                 105                 110

Ala Glu Gly Phe Leu Ala Glu Glu Lys Gln Leu His Ile Leu Ile Asn
        115                 120                 125

Asn Ala Gly Val Met Met Cys Pro Tyr Ser Lys Thr Ala Asp Gly Phe
    130                 135                 140

Glu Thr His Leu Gly Val Asn His Leu Gly His Phe Leu Leu Thr Tyr
145                 150                 155                 160

Leu Leu Leu Glu Arg Leu Lys Val Ser Ala Pro Ala Arg Val Val Asn
                165                 170                 175

Val Ser Ser Val Ala His His Ile Gly Lys Ile Pro Phe His Asp Leu
            180                 185                 190

Gln Ser Glu Lys Arg Tyr Ser Arg Gly Phe Ala Tyr Cys His Ser Lys
        195                 200                 205

Leu Ala Asn Val Leu Phe Thr Arg Glu Leu Ala Lys Arg Leu Gln Gly
    210                 215                 220

Thr Gly Val Thr Thr Tyr Ala Val His Pro Gly Val Val Arg Ser Glu
225                 230                 235                 240

Leu Val Arg His Ser Ser Leu Leu Cys Leu Leu Trp Arg Leu Phe Ser
                245                 250                 255

Pro Phe Val Lys Thr Ala Arg Glu Gly Ala Gln Thr Ser Leu His Cys
            260                 265                 270

Ala Leu Ala Glu Gly Leu Glu Pro Leu Ser Gly Lys Tyr Phe Ser Asp
        275                 280                 285

Cys Lys Arg Thr Trp Val Ser Pro Arg Ala Arg Asn Asn Lys Thr Ala
    290                 295                 300

Glu Arg Leu Trp Asn Val Ser Cys Glu Leu Leu Gly Ile Arg Trp Glu
305                 310                 315                 320

<210> SEQ ID NO 5
<211> LENGTH: 949
<212> TYPE: DNA
<213> ORGANISM: Artificial Sequence
<220> FEATURE:
<223> OTHER INFORMATION: RDH12 coding sequence

<400> SEQUENCE: 5

| | | | | |
|---|---|---|---|---|
| atgttggtca | ccctcggact | ccttacctca | tttttctcct | tcctgtacat ggtcgccccg | 60 |
| agcattagaa | agttcttcgc | cggcggagtg | tgtaggacta | acgtgcagtt gcccgggaag | 120 |
| gtcgtggtga | ttactggcgc | caacactggt | atcggaaagg | aaactgcgcg ggaactggcg | 180 |
| tccagaggtg | cccgcgtgta | cattgcatgc | cgcgacgtgc | tgaagggaga atccgccgcg | 240 |
| tccgagatcc | gggtggacac | caaaaatagc | caggtgctcg | tgcggaagct ggatctgtcc | 300 |
| gacaccaagt | caatcagggc | cttttgccgag | gggttcctgg | ctgaagagaa gcagctccac | 360 |
| attctgatca | acaacgccgg | ggtcatgatg | tgccccctact | caaagaccgc agacggcttc | 420 |
| gaaacccacc | tgggcgtgaa | ccatctggga | cacttcctgc | tgacctatct gctgctggag | 480 |
| cgactgaaag | tgtcggctcc | tgctcgggtc | gtgaacgtgt | ccagcgtggc ccatcacatc | 540 |
| ggaaagatcc | cattccacga | tctccaatcc | gagaagcggt | acagcagggg cttcgcgtac | 600 |
| tgtcactcga | agttggccaa | cgtgctcttt | acccgcgaac | tggccaagcg gctgcagggc | 660 |
| actggcgtga | ccacttacgc | cgtgcaccct | ggtgtcgtgc | ggtccgagct ggtccgccat | 720 |
| tcctctcttc | tgtgcctcct | gtggagactc | ttctccccgt | tcgtcaagac cgcaagggaa | 780 |
| ggagcccaaa | cgagccttca | ctgtgccctg | gcggaaggac | tggagccgct tagcggaaag | 840 |

```
tacttctcgg actgcaagcg cacctgggtg tcgcctagag ctcggaacaa caagactgcc      900
gaacgcctct ggaatgtgtc ctgcgagctg ctgggaatca gatgggagt                 949
```

METHODS AND COMPOSITIONS FOR TREATMENT OF DISORDERS AND DISEASES INVOLVING RDH12

CROSS-REFERENCE TO RELATED APPLICATIONS

This is a US National Stage of International Patent Application No. PCT/US2017/041122, filed Jul. 7, 2017, which claims the benefit of U.S. Provisional Patent Application No. 62/359,777 filed Jul. 8, 2016. These applications are incorporated by reference herein.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-16-7699PCT_ST25.txt", having a size of 9 kB and dated Jul. 5, 2017.

BACKGROUND OF THE INVENTION

Retinoid dehydrogenases/reductases located in the photoreceptor cells and the RPE catalyze important oxidation-reduction reactions in the visual cycle. RDH12 retinol dehydrogenase 12 (all-trans/9-cis/11-cis) (14-23.3-q24.1) (MIM no. 608830) encodes a dual specificity enzyme expressed in the retina that acts on both trans and cis retinoid substrates. See, e.g., Thompson, D A et al, November 2005, Human Mol. Genet., 14(24):3865-3875. A number of mutations in human RDH12 have been associated with certain forms of severe, childhood-onset autosomal recessive retinal dystrophy (arRD). For example, defects in this gene are a cause of Leber congenital amaurosis type 13 and Retinitis Pigmentosa 53.

Leber's Congenital Amaurosis (LCA), a severe dystrophy of the retina, affects about 1 in 80,000 people worldwide. The disorder is autosomal recessive and carriers present with abnormal development of photoreceptors at birth or within the first few months of life. Abnormalities result in severe vision impairment and blindness. RDH12-associated LCA is one of the rarer forms of LCA. Only about 2.7% of the LCA cases are caused by a mutation in RDH12.

Retinitis pigmentosa (RP) 53 is another retinal dystrophy belonging to the group of pigmentary retinopathies. Retinitis pigmentosa is characterized by retinal pigment deposits visible on fundus examination and primary loss of rod photoreceptor cells followed by secondary loss of cone photoreceptors. Patients typically have night vision blindness and loss of midperipheral visual field. As their condition progresses, they lose their far peripheral visual field and eventually central vision as well. RDH12 is also associated with this blinding disease.

Current treatment of these blinding diseases is primarily supportive, involving referral of patients to programs for the visually impaired child, correction of refractive error and use of low-vision aids, when possible, and access to occupational/educational therapies. Periodically affected pateints receive ophthalmic evaluation and, in those with residual vision, are examined for the presence of amblyopia, glaucoma, or cataract, with appropriate therapies. Gene augmentation therapies are being evaluated for the treatment of certain forms of Leber's congenital amaurosis (LCA). See, e.g., U.S. Pat. No. 8,147,823.

A continuing need in the art exists for new and effective tools and methods for successful treatment of LCA13, RP53 and other ocular diseases.

SUMMARY OF THE INVENTION

Therapeutic compositions and methods useful in the treatment of ocular disorders involve novel cDNA sequences optimized to encode functional RDH12 protein and the delivery of the optimized sequences to a subject with an ocular disease. In one embodiment, such novel sequences include plasmid sequences capable of being packaged in viral vectors. In other embodiments, novel AAV proviral plasmids and/or recombinant AAV are provided to carry the optimized sequences. As discussed herein, these vectors have demonstrated biological activities both in vitro and in vivo.

In one aspect, a codon optimized cDNA sequence encoding a functional mammalian, preferably human, RDH12 is provided.

In another aspect an expression cassette comprises a codon optimized nucleic acid sequence that encodes one or more functional copies of RDH12. In one embodiment, an expression cassette further comprises a codon optimized nucleic acid sequence that encodes one or more functional copies of RDH12 operably linked and under the control of regulatory sequences directing its expression in a host cell, positioned between 5' and 3' AAV ITR sequences.

In other aspects, a vector is provided that contains one or more of the expression cassettes described herein and host cells are provided that contain the vectors or expression cassettes.

In another aspect, a proviral plasmid comprises sequences encoding an AAV capsid, AAV inverted terminal repeat sequences and an expression cassette comprising a codon optimized nucleic acid sequence that encodes native or mutated or codon optimized RDH12 and expression control sequences that direct expression of the encoded protein in a host cell. In certain embodiments, the plasmid components are modular.

In another embodiment, a recombinant adeno-associated virus (AAV) comprises an AAV capsid protein and a nucleic acid sequence encoding a functional RDH12 protein, or fragment thereof, under the control of regulatory sequences which express the RDH12 in the photoreceptor cells of a subject. In one embodiment, the rAAV comprises an AAV8 capsid or variant thereof, or an AAV7 capsid or variant thereof, or an AAV2 capsid or variant thereof, or an AAV5 capsid or variant thereof.

In another embodiment, an rAAV comprises AAV inverted terminal repeat sequences and an expression cassette comprising a codon optimized nucleic acid sequence that encodes functional RDH12 and expression control sequences that direct expression of the encoded protein in a host cell.

In yet a further aspect a pharmaceutical composition comprises a pharmaceutically acceptable carrier, diluent, excipient and/or adjuvant and the optimized nucleic acid sequence encoding functional RDH12, and a plasmid, a vector, or a viral vector, such as the rAAV, described specifically herein. In one embodiment, the optimized nucleic acid sequence is under the control of regulatory sequences which express the functional RDH12 in the photoreceptor cells of a subject. In one embodiment, the composition contains multiple copies of sequences encoding functional RDH12. In another embodiment, the composition includes a pharmaceutically acceptable carrier.

In a further aspect, a cell is provided that expresses functional RDH12 protein encoded by a codon-optimized RDH12 cDNA. In one embodiment, such a cell is an induced pluripotent stem cell (iPSC) which has treated by gene editing systems such as Crispr/Cas9 system and related systems and components to target and correct mutations in the cell's existing RDH12 sequences or to insert RDH12 codon optimized sequences for novel expression in that cell.

In another aspect, a method of treating an RDH12-mediated disorder in a mammalian subject comprises administering to a subject in need thereof the codon-optimized RDH12 cDNA described herein, or a vector, virus or pharmaceutical compositions as described herein.

In another aspect, a method for treating, retarding or halting progression of blindness, or restoring at least partial vision, in a mammalian subject comprises administering or delivering to the subject an optimized nucleic acid sequence or fragment thereof encoding a functional RDH12 protein, or fragment thereof. In one embodiment, the method utilizes any of the compositions described herein.

In another aspect, a method for treating, retarding or halting progression of blindness or restoring at least partial vision in a mammalian subject comprises administering a recombinant adeno-associated virus (AAV) comprising an AAV capsid protein and a nucleic acid sequence encoding a functional RDH12 protein, or fragment thereof, under the control of regulatory sequences which express the RDH12 in the photoreceptor cells of a subject and a pharmaceutically acceptable carrier. In one embodiment, the method utilizes any of the compositions described herein.

In still another aspect, a method to treat an ocular disorder resulting from expression of non-functional or improperly functional RDH12 or inadequate amounts or deficiencies of RDH12 comprises administering to a subject with the deficiency a vector comprising a native or codon-optimized RDH12 gene under the control of a suitable promoter.

In still another aspect, a method to treat RDH12 deficiency or RDH12 mutation-associated disorder comprises employing gene editing systems such as Crispr/Cas9 system and related systems and components to target and correct mutations in RDH12. In one embodiment, the correction involves optimizing the RDH12 encoding sequence in vivo.

In another embodiment, a method of treating or preventing LCA or RP caused by a defect, deficiency or mutation in RDH12 in a subject in need thereof is provided. The method includes (a) identifying a subject having, or at risk of developing, RDH12-associated LCA or RP; (b) performing genotypic analysis and identifying a mutation in the RDH12 gene; (c) performing non-invasive retinal imaging and functional studies and identifying areas of retained photoreceptors that could be targeted for therapy; (d) administering to the subject an effective concentration of a composition comprising a vector (e.g., a recombinant virus) carrying a nucleic acid sequence encoding a functional RDH12 under the control of a promoter sequence which expresses the product of said sequence in said photoreceptor cells, and a pharmaceutically acceptable carrier, wherein said disorder is prevented, arrested or ameliorated.

Still other aspects and advantages of these compositions and methods are described further in the following detailed description of the preferred embodiments thereof.

BRIEF DESCRIPTION OF THE DRAWINGS

FIGS. 1A-1B are an alignment of codon optimized RDH12 (SEQ ID NO: 5; top sequence) with native RDH12 (SEQ ID NO: 1; bottom sequence) showing about 78% sequence similarity. In this alignment, the score is 787 bits (872), the identities are 744/949 (78%); the gaps are 0/949 (0%); and the two strands are plus strands.

FIGS. 6A-6D show experimental results for a single animal 136 in which the left eye (FIGS. 6A AND 6C) was uninjected. The right eye (FIGS. 6B and 6D) was injected with AAV7m8-RDH12-Myc. ERG baseline was performed followed by light damage, followed by a second ERG. The animals were housed for 10 days and a third ERG was performed. Mice were sacrificed and eyes collected fixed and sectioned and stained with DAPI (FIGS. 6A and 6B) or with rhodopsin and DAPI (FIGS. 6C and 6D).

FIG. 7A shows the left uninjected eye. FIG. 7B shows a higher magnification image of the left eye, showing a thin ONL. FIG. 7C is a right eye injected with AAV7m8-RDH12-Myc.

FIG. 8A shows the retinal architecture of an animal with a left eye uninjected showing a thin retina. FIG. 8B shows the animal's right eye, injected with AAV8-RDH12-Myc.

FIGS. 9A and 9B show the retinal architecture of a single animal 147 with higher magnification images. FIG. 9A shows uninjected left eye. FIG. 9B shows right eye injected with AAV8-RDH12-Myc.

DETAILED DESCRIPTION

Figure 2A:
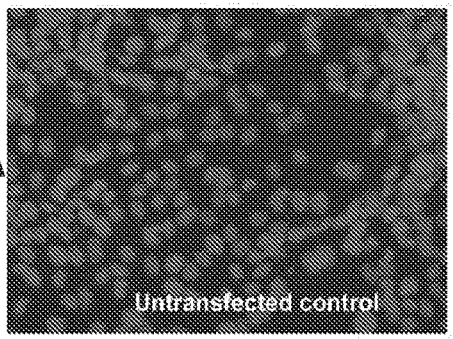
FIGS. 2A-2F are 6 panels of showing the expression of the RDH12 plasmid: left (FIG. 2A) and right (FIG. 2B) top panels show untransfected control; left (FIG. 2C) and right (FIG. 2D) middle panels show RDH12Myc transfected cells; left bottom panel shows RDH12Myc transfected cells (FIG. 2E); right bottom panel (FIG. 2F) is an enlargement of two cells from the right middle panel (FIG. 2D).

The methods and compositions described herein are useful for the treatment of ocular disorders. Such ocular disorders are RDH12-mediated disorders or diseases, e.g., disorders, caused by, or involving a mutation, defect or deficiency in the gene encoding human retinal dehydrogenase 12 (RDH12). In one embodiment, these compositions and methods are useful in delivering a codon optimized cDNA encoding functional human retinal dehydrogenase gene (hRDH12) to mammalian subjects for the treatment of ocular disorders. In certain embodiments, the RDH12-mediated disorder is a blinding disease such as LCA or LCA13, or RP or RP53. In other embodiments, the methods and compositions are useful in editing the subject's defective gene in vivo or in creating a suitable cell line expressing the codon optimized cDNA sequence encoding functional RDH12 using gene editing systems such as the CRISPR/Cas system. The compositions and methods described herein involve expression cassettes, vectors, recombinant viruses and other compositions for delivery of one or multiple, different versions of the sequence encoding a functional RDH12. Such compositions involve both codon optimization and the assembly of multiple and or different versions of RDH12 in the same expression cassette, vector or virus. These features not only increase the efficacy of the functional RDH12 protein being expressed, but may also permit a lower dose of a therapeutic reagent that delivers the functional protein to increase safety. It is anticipated that optimization of the nucleic acid sequence encoding RDH12 delivered in a cassette or virus maximizes the level of production of functional RDH12 protein in vivo, compared to levels that can be generated using the native or endogenous sequence encoding RDH12.

Technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention.

The terms "a" or "an" refers to one or more. For example, "an expression cassette" is understood to represent one or more such cassettes. As such, the terms "a" (or "an"), "one or more," and "at least one" are used interchangeably herein.

As used herein, the term "about" means a variability of plus or minus 10% from the reference given, unless otherwise specified.

The words "comprise", "comprises", and "comprising" are to be interpreted inclusively rather than exclusively, i.e., to include other unspecified components or process steps. The words "consist", "consisting", and its variants, are to be interpreted exclusively, rather than inclusively, i.e., to exclude components or steps not specifically recited.

"RDH12" is retinol dehydrogenase 12 (all-trans/9-cis/11-cis) protein, preferably the human ortholog thereof. This protein is also known as RP53, LCA13 and SDR7C2. The term "RDH12" as used herein, refers to the full length protein itself or a functional fragment, or variant thereof, as further defined below. In one embodiment, the RDH12 protein sequence is derived from the same mammal that the composition is intended to treat. In one embodiment, the RDH12 is derived from a human. In another embodiment, the RDH12 is derived from a canine.

By the term "fragment" or "functional fragment" when applied to a protein, refers to any fragment that retains the function of the full length protein, although not necessarily at the same level of expression or activity.

By "functional protein" is meant any amino acid sequence that demonstrates the biological activity of a normally functioning protein, e.g., RDH12, in a subject with no ocular disorder or disease. Such a functional protein can carry mutations or modifications of its encoding DNA sequence or within its amino acid sequence, which mutations do not cause ocular disease or disorders. In an other embodiment, such a functional protein can include mutations or which cause the protein to perform its functions better than a "native" or endogenous sequence. In one embodiment, such a functional RDH12 protein can be considered a normal or normally-functioning protein.

In one embodiment, a native human RDH12 has the following sequence labeled SEQ ID NO: 2 (which is the encoded protein of the nucleic acid sequence SEQ ID NO: 1, reported in the section B below):

MLVTLGLLTSFFSFLYMVAPSIRKFFAGGVCRTNVQLPGKVVVITGANTGI

GKETARELASRGARVYIACRDVLKGESAASEIRVDTKNSQVLVRKLDLSDT

KSIRAFAEGFLAEEKQLHILINNAGVMMCPYSKTADGFETHLGVNHLGHFL

LTYLLLERLKVSAPARVVNVSSVAHHIGKIPFHDLQSEKRYSRGFAYCHSK

LANVLFTRELAKRLQGTGVTTYAVHPGVVRSELVRHSSLLCLLWRLFSPFV

KTAREGAQTSLHCALAEGLEPLSGKYFSDCKRTWVSPRARNNKTAERLWNV

SCELLGIRWE.

In another embodiment, the RDH12 protein sequence is a variant which shares at least 70, at least 75%, at least 78% or at least 80% identity with a native RDH12 protein, such as SEQ ID NO: 1. In another embodiment, the RDH12 protein sequence shares at least 85% identity with a native RDH12 protein. In another embodiment, the RDH12 protein sequence shares at least 90% identity with a native RDH12 protein. In another embodiment, the RDH12 protein sequence shares at least 91% identity with a native RDH12 protein. In another embodiment, the RDH12 protein sequence shares at least 92% identity with a native RDH12 protein. In another embodiment, the RDH12 protein sequence shares at least 93% identity with a native RDH12 protein. In another embodiment, the RDH12 protein sequence shares at least 94% identity with a native RDH12 protein. In another embodiment, the RDH12 protein sequence shares at least 95% identity with a native RDH12 protein. In another embodiment, the RDH12 protein sequence shares at least 96% identity with a native RDH12 protein. In another embodiment, the RDH12 protein sequence shares at least 97% identity with a native RDH12 protein. In another embodiment, the RDH12 protein sequence shares at least 98% identity with a native RDH12 protein. In another embodiment, the RDH12 protein sequence shares at least 99% identity with a native RDH12 protein.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 70 amino acids to about 300 amino acids, or a peptide fragment thereof or the corresponding nucleic acid sequence coding sequencers. A suitable amino acid fragment may be at least about 8 amino acids in length, and may be up to about 150 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another method which provides at least the level of identity or alignment as that provided by the referenced methods. See, e.g., J. D. Thomson et al, Nucl. Acids. Res., "A comprehensive comparison of multiple sequence alignments", 27(13):2682-2690 (1999).

By "optimized" or "codon-optimized" RDH12 protein is meant an RDH12 protein sequence encoded by a DNA sequence which differs from the native or naturally occurring sequence, such as that of SEQ ID NO: 1, by codon changes that make silent, conservative or non-conservative amino acid changes, or amino acid insertions or deletions in the protein. These changes may increase protein production and/or enhance protein confirmation and stability. An optimized RDH12 protein as described herein is a functional RDH12 protein encoded by a codon-optimized DNA sequence.

One embodiment of an optimized RDH12 protein is the translated functional RDH12 protein sequence labeled SEQ ID NO: 4 (which is the encoded protein of the nucleic acid sequence SEQ ID NO: 3, reported in the section B below):

AAATMLVTLGLLTSFFSFLYMVAPSIRKFFAGGVCRTNVQLPGKVVVITGA

NTGIGKETARELASRGARVYIACRDVLKGESAASEIRVDTKNSQVLVRKLD

LSDTKSIRAFAEGFLAEEKQLHILINNAGVMMCPYSKTADGFETHLGVNHL

GHFLLTYLLLERLKVSAPARVVNVSSVAHHIGKIPFHDLQSEKRYSRGFAY

CHSKLANVLFTRELAKRLQGTGVTTYAVHPGVVRSELVRHSSLLCLLWRLF

SPFVKTAREGAQTSLHCALAEGLEPLSGKYFSDCKRTWVSPRARNNKTAER

LWNVSCELLGIRWE.

As above synonymous codon changes or codon changes resulting in conservative amino acid changes, or insertions or deletions can increase protein production and/or enhance protein confirmation and stability. Such optimization is useful for development of therapeutic reagents that maximize the level of production of the experimental protein compared to levels that can be generated using the endogenous or native sequence.

The nucleic acid sequence encoding a normal or normally functional RDH12 protein may be derived from any mammal which natively expresses the RDH12 protein, or homolog thereof. In one embodiment, a native nucleic acid sequence encoding human RDH12, is reported at NCBI database accession No. NC_000014.9.

In one embodiment, a native human RDH12 DNA sequence is labeled SEQ ID NO: 1:

ATGCTGGTCACCTTGGGACTGCTCACCTCCTTCTTCTCGTTCCTGTATATG

GTAGCTCCATCCATCAGGAAGTTCTTTGCTGGTGGAGTGTGTAGAACAAAT

GTGCAGCTTCCTGGCAAGGTAGTGGTGATCACTGGCGCCAACACGGGCATT

GGCAAGGAGACGGCCAGAGAGCTCGCTAGCCGAGGAGCCCGAGTCTATATT

GCCTGCAGAGATGTACTGAAGGGGGAGTCTGCTGCCAGTGAAATCCGAGTG

GATACAAAGAACTCCCAGGTGCTGGTGCGGAAATTGGACCTATCCGACACC

AAATCTATCCGAGCCTTTGCTGAGGGCTTTCTGGCAGAGGAAAAGCAGCTC

CATATTCTGATCAACAATGCGGGAGTAATGATGTGTCCATATTCCAAGACA

GCTGATGGCTTTGAAACCCACCTGGGAGTCAACCACCTGGGCCACTTCCTC

CTCACCTACCTGCTCCTGGAGCGGCTAAAGGTGTCTGCCCCTGCACGGGTG

GTTAATGTGTCCTCGGTGGCTCACCACATTGGCAAGATTCCCTTCCACGAC

CTCCAGAGCGAGAAGCGCTACAGCAGGGGTTTTGCCTATTGCCACAGCAAG

CTGGCCAATGTGCTTTTTACTCGTGAGCTGGCCAAGAGGCTCCAAGGCACC

GGGGTCACCACCTACGCAGTGCACCCAGGCGTCGTCCGCTCTGAGCTGGTC

CGGCACTCCTCCCTGCTCTGCCTGCTCTGGCGGCTCTTCTCCCCCTTTGTC

AAGACGGCACGGGAGGGGCGCAGACCAGCCTGCACTGCGCCCTGGCTGAG

GGCCTGGAGCCCCTGAGTGGCAAGTACTTCAGTGACTGCAAGAGGACCTGG

GTGTCTCCAAGGGCCCGAAATAACAAAACAGCTGAGCGCCTATGGAATGTC

AGCTGTGAGCTTCTAGGAATCCGGTGGGAGT

In other embodiments, certain modifications are made to the RDH12 coding sequence in order to enhance the expression in the target cell. Such modifications include codon optimization, (see, e.g., U.S. Pat. Nos. 7,561,972; 7,561,973; and 7,888,112, incorporated herein by reference) and conversion of the sequence surrounding the translational start site to a consensus Kozak sequence: gccRccATGR. See, Kozak et al, *Nucleic Acids Res.* 15 (20): 8125-8148, incorporated herein by reference. A codon-optimized nucleic acid sequence differs from the native or naturally occurring sequence, such as that of SEQ ID NO: 1, by synonymous codon changes that increase protein production, expression and/or enhance protein confirmation and stability.

Codon-optimized coding regions can be designed by various different methods. This optimization may be performed using methods which are available on-line, published methods, or a company which provides codon optimizing services. One codon optimizing method is described, e.g., in International Patent Application Pub. No. WO 2015/012924, which is incorporated by reference herein. Briefly, the nucleic acid sequence encoding the product is modified with synonymous codon sequences. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide. Such optimization is useful for development of gene therapy reagents that maximize the level of production of the experimental protein compared to levels that can be generated using the endogenous or native sequence. Such codon-optimized sequences may in one embodiment increase the efficacy of the resulting therapeutic reagent compositions, but also permit a lower dose of reagent to be used, thus increasing therapeutic safety.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

One embodiment of a codon-optimized RDH12 DNA sequence is the RDH12 DNA sequence labeled SEQ ID NO: 3.

GCGGCCGCCACCATGTTGGTCACCCTCGGACTCCTTACCTCATTTTTCTCC

TTCCTGTACATGGTCGCCCCGAGCATTAGAAAGTTCTTCGCCGGCGGAGTG

TGTAGGACTAACGTGCAGTTGCCCGGGAAGGTCGTGGTGATTACTGGCGCC

AACACTGGTATCGGAAAGGAAACTGCGCGGGAACTGGCGTCCAGAGGTGCC

CGCGTGTACATTGCATGCCGCGACGTGCTGAAGGGAGAATCCGCCGCGTCC

GAGATCCGGGTGGACACCAAAAATAGCCAGGTGCTCGTGCGGAAGCTGGAT

CTGTCCGACACCAAGTCAATCAGGGCCTTTGCCGAGGGGTTCCTGGCTGAA

GAGAAGCAGCTCCACATTCTGATCAACAACGCCGGGGTCATGATGTGCCCC

TACTCAAAGACCGCAGACGGCTTCGAAACCCACCTGGGCGTGAACCATCTG

GGACACTTCCTGCTGACCTATCTGCTGCTGGAGCGACTGAAAGTGTCGGCT

CCTGCTCGGGTCGTGAACGTGTCCAGCGTGGCCCATCACATCGGAAAGATC

CCATTCCACGATCTCCAATCCGAGAAGCGGTACAGCAGGGGCTTCGCGTAC

TGTCACTCGAAGTTGGCCAACGTGCTCTTTACCCGCGAACTGGCCAAGCGG

CTGCAGGGCACTGGCGTGACCACTTACGCCGTGCACCCTGGTGTCGTGCGG

TCCGAGCTGGTCCGCCATTCCTCTCTTCTGTGCCTCCTGTGGAGACTCTTC

TCCCCGTTCGTCAAGACCGCAAGGGAAGGAGCCCAAACGAGCCTTCACTGT

GCCCTGGCGGAAGGACTGGAGCCGCTTAGCGGAAAGTACTTCTCGGACTGC

AAGCGCACCTGGGTGTCGCCTAGAGCTCGGAACAACAAGACTGCCGAACGC

CTCTGGAATGTGTCCTGCGAGCTGCTGGGAATCAGATGGGAGTGATGATCA

TGAGATCT

When aligned with the native nucleic acid sequence encoding human RDH12, a codon optimized RDH12-encoding sequence may have a percent identity of at least 50%, or at least 60%, or at least 70%, or at least 80% or at least 90%, including any integer between any of those ranges. In one embodiment, the codon optimized RDH12 has a percent identify with the native sequence of at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%.

The terms "percent (%) identity", "sequence identity", "percent sequence identity", or "percent identical" in the context of nucleic acid sequences refers to the bases in the two sequences which are the same when aligned for correspondence. The percent identity is determined by comparing two sequences aligned under optimal conditions over the sequences to be compared. The length of sequence identity comparison may be over the full-length of the RDH12 coding sequence, or a fragment of at least about 100 to 150 nucleotides, or as desired. However, identity among smaller fragments, e.g. of at least about nine nucleotides, usually at least about 20 to 24 nucleotides, at least about 28 to 32 nucleotides, at least about 36 or more nucleotides, may also be desired. Multiple sequence alignment programs are also available for nucleic acid sequences. Examples of such programs include, "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of methods known in the art that can be used to measure nucleotide sequence identity, including those contained in the programs described above. As another example, polynucleotide sequences can be compared using Fasta™, a program in GCG Version 6.1. Commonly available sequence analysis software, more specifically, BLAST or analysis tools provided by public databases may also be used.

In the embodiment of SEQ ID NO: 3, the cDNA of a native human RDH12 was modified by the inventors by adding a complete Kozak consensus at the 5' end embedded in a NotI site and by adding MI and BamHI sites at the 3' end (restriction sites for cloning). A TGA stop codon was embedded in the WI site to facilitate optimal epitope tagging. This embodiment also avoids the use of certain internal restriction enzymes such as BglII, Bsu36I, NheI, NotI, SalI and XhoI. A NotI restriction site with a Kozak-CACC sequence is inserted at nucleotide 1-12 of SEQ ID NO: 3. A BglII restriction site is inserted at the last six nucleotides of SEQ ID NO: 3.

Specifically FIGS. 1A-1B show a sequence alignment of SEQ ID NO: 5 (codon-optimized RDH12 DNA sequence) with SEQ ID NO: 1 (native RDH12 coding sequence). The open reading frame of codon optimized RDH12 differs from the native sequence by 22% of the nucleotides (i.e. 78% homology), although the resulting encoded protein is the same.

As used herein, the term "subject" as used herein means a mammalian animal, including a human, a veterinary or farm animal, a domestic animal or pet, and animals normally used for clinical research. In one embodiment, the subject of these methods and compositions is a human. Still other suitable subjects include, without limitation, murine, rat, canine, feline, porcine, bovine, ovine, and others. As used herein, the term "subject" is used interchangeably with "patient". The subject includes any mammal in need of these methods of treatment or prophylaxis, including particularly humans. The subject may be male or female. In one embodiment, the subject has, or is at risk of developing, Leber congenital amaurosis (LCA) or retinitis pigmentosa. In another embodiment, the subject has or is at risk of developing LCA or RP or other ocular disorder associated with a mutation in, or lack of, or inadequately expressed functional RDH12. In another embodiment, the subject has shown clinical signs of LCA or RP. Clinical signs of LCA or RP include, but are not limited to, nystagmus, decreased peripheral vision, decreased central (reading) vision, decreased night vision, loss of color perception, reduction in visual acuity, decreased photoreceptor function, pigmentary changes and blindness. In another embodiment, the subject has been diagnosed with LCA or RP. In yet another embodiment, the subject has not yet shown clinical signs of LCA or RP.

In yet another embodiment, the subject has about or at least 5 to 10% photoreceptor damage and/or loss. In another embodiment, the subject has at least 20% photoreceptor damage and/or loss. In another embodiment, the subject has at least 30% photoreceptor damage and/or loss. In another embodiment, the subject has at least 40%, at least 50%, at least 60% photoreceptor damage/loss. In another embodiment, the subject has at least 70%, at least 80%, or at least 90% photoreceptor damage and/or loss. In one another embodiment, the subject has about or at least 5 to 10% or more rod and/or cone function damage/loss. In one another embodiment, the subject has at least 20% rod and/or cone function damage/loss. In one another embodiment, the subject has at least 30% rod and/or cone function damage/loss. In one another embodiment, the subject has at least 40% rod and/or cone function damage/loss. In one another embodiment, the subject has at least 50% rod and/or cone function damage/loss. In one another embodiment, the subject has at least 60%, at least 70%, at least 80% rod and/or cone function damage/loss. In one another embodiment, the subject has 90% rod and/or cone function damage/loss.

As used herein, the term "disorder" or "genetic disorder" or "RDH12-mediated disorder" is used throughout this specific to refer to any diseases, disorders, or conditions associated with an insertion, change or deletion in the amino acid sequence of the native (e.g., wild-type) RDH12 protein which renders the RDH12 protein either partially or wholly non-functional in the subject's ocular cells. The disorder or genetic disease can also involve some other defect which renders the RDH12 protein either partially or wholly non-functional or partially or wholly expressed in the subject's ocular cells. Unless otherwise specified such disorders include inherited and/or non-inherited genetic disorders, as well as diseases and conditions which may not manifest physical symptoms during infancy or childhood.

As used herein, the term "ocular cells" refers to any cell in, or associated with the function of, the eye. The term may refer to any one or more of photoreceptor cells, including rod, cone and photosensitive ganglion cells, retinal pigment epithelium (RPE) cells, Mueller cells, bipolar cells, horizontal cells, amacrine cells. In one embodiment, the ocular cells are the photoreceptor cells. In another embodiment, the ocular cells are the rod and cone cells. In yet another embodiment, the ocular cells are the cone cells.

In certain embodiments of this invention, a subject has an "ocular disorder", for which the components, compositions and methods of this invention are designed to treat. As used herein "ocular disorder" includes, rod-cone dystrophies and retinal diseases including, without limitation, Stargardt disease (autosomal dominant or autosomal recessive), retinitis pigmentosa, age-related macular degeneration, rod-cone dystrophy, Leber's congenital amaurosis, Usher's syndrome, Bardet-Biedl Syndrome, Best disease, Bassen-Kornzweig syndrome, retinoschisis, untreated retinal detachment, pattern dystrophy, achromatopsia, choroideremia, ocular albinism, enhanced S cone syndrome, diabetic retinopathy, retinopathy of prematurity, sickle cell retinopathy, refsun syndrome, Congenital Stationary Night Blindness, glaucoma, gyrate atrophy or retinal vein occlusion. In another embodiment, the subject has, or is at risk of developing glaucoma, Leber's hereditary optic neuropathy, lysosomal storage disorder, or peroxisomal disorder. Clinical signs of such ocular diseases include, but are not limited to, decreased peripheral vision, decreased central (reading) vision, decreased night vision, loss of color perception, reduction in visual acuity, decreased photoreceptor function, pigmentary changes, and ultimately blindness.

In certain embodiments of this invention, the RDH12 nucleic acid sequence, is delivered to the ocular cells in need of treatment by means of a vector or a viral vector, of which many are known and available in the art. For delivery to the ocular cells, the therapeutic vector is desirably non-toxic, non-immunogenic, easy to produce, and efficient in protecting and delivering DNA into the target cells. A "vector" as used herein is a nucleic acid molecule into which an exogenous or heterologous or engineered nucleic acid sequence or transgene may be inserted which can then be introduced into an appropriate host cell. Vectors preferably have one or more origin of replication, and one or more site into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes."

The term "exogenous" as used to describe a nucleic acid sequence or protein means that the nucleic acid or protein does not naturally occur in the position in which it exists in a chromosome, recombinant plasmid, vector or host cell. An exogenous nucleic acid sequence also refers to a sequence derived from and inserted into the same host cell or subject, but which is present in a non-natural state, e.g. a different copy number, or under the control of different regulatory elements.

The term "heterologous" as used to describe a nucleic acid sequence or protein means that the nucleic acid or protein was derived from a different organism or a different species of the same organism than the host cell or subject in which it is expressed. The term "heterologous" when used with reference to a protein or a nucleic acid in a plasmid, expression cassette, or vector, indicates that the protein or the nucleic acid is present with another sequence or subsequence which with which the protein or nucleic acid in question is not found in the same relationship to each other in nature.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated, even if subsequently reintroduced into the natural system. Such polynucleotides could be part of a vector and/or such polynucleotides or polypeptides could be part of a composition, and still be isolated in that such vector or composition is not part of its natural environment.

By "engineered" is meant that the nucleic acid sequences encoding the RDH12 and RDH12 proteins described herein are assembled and placed into any suitable genetic element, e.g., naked DNA, phage, transposon, cosmid, episome, etc., which transfers the RDH12 sequences carried thereon to a host cell, e.g., for generating non-viral delivery systems (e.g., RNA-based systems, naked DNA, or the like) or for generating viral vectors in a packaging host cell and/or for delivery to a host cells in a subject. In one embodiment, the genetic element is a plasmid. The methods used to make such engineered constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

"Virus vectors" are defined as replication defective, synthetic, or recombinant viral particles containing the exogenous or heterologous nucleic acid sequence encoding the functional RDH12. In one embodiment, an expression cassette as described herein may be engineered onto a plasmid which is used for drug delivery or for production of a viral vector. Suitable viral vectors are preferably replication defective and selected from amongst those which target ocular cells. In one embodiment, an expression cassette containing a transgene is packaged in a viral capsid or envelope. Any viral genomic sequences also packaged within that viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

Viral vectors may include any virus suitable for gene therapy, including but not limited to adenovirus; herpes virus; lentivirus; retrovirus; parvovirus, etc. However, for ease of understanding, the adeno-associated virus is referenced herein as an exemplary virus vector. Thus, in one embodiment, a therapeutic composition or reagent comprises an adeno-associated viral vector comprising an RDH12 transgene operatively linked to expression control sequences. The term "transgene" as used herein means an exogenous or engineered protein-encoding nucleic acid sequence that is under the control of a promoter or expression control sequence in an expression cassette (with or without flanking rAAV ITRs), recombinant plasmid or proviral plasmid, vector, or host cell described in this specification. In certain embodiments, the transgene is a codon optimized RDH12 encoding sequence SEQ ID NO: 3. In certain embodiments, the transgene is a naturally occurring or native RDH12 encoding sequence SEQ ID NO:1. In other embodiments, both codon optimized and natural RDH12 encoding sequences, in various combinations can serve as the transgene.

As used herein, the term "operably linked" or "operatively associated" refers to both expression control sequences that are contiguous with the nucleic acid sequence encoding the RDH12 and/or expression control sequences that act in trans or at a distance to control the transcription and expression thereof.

As used herein, the term "host cell" may refer to the packaging cell line in which a recombinant AAV is produced from a proviral plasmid. In the alternative, the term "host cell" may refer to any target cell in which expression of the transgene is desired. Thus, a "host cell," refers to a prokaryotic or eukaryotic cell that contains exogenous or heterologous DNA that has been introduced into the cell by any means, e.g., electroporation, calcium phosphate precipitation, microinjection, transformation, viral infection, transfection, liposome delivery, membrane fusion techniques, high velocity DNA-coated pellets, viral infection and protoplast fusion. In certain embodiments herein, the term "host cell" refers to cultures of ocular cells of various mammalian species for in vitro assessment of the compositions described herein. In other embodiments herein, the term "host cell" refers to the cells employed to generate and package the viral vector or recombinant virus. Still in other embodiments, the term "host cell" is intended to reference the ocular cells of the subject being treated in vivo for the ocular disease. In yet another embodiment, the host cell can refer to induced pluripotent stem cells (iPSCs), which are adult cells that have been genetically reprogrammed to an embryonic stem cell-like state by being forced to express genes and factors important for maintaining the defining properties of embryonic stem cells. Such cells can be manipulated and used as models or tools for assessing the function of the vectors described herein.

"Plasmids" or plasmid vectors generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

As used herein, the term "transcriptional control sequence" or "expression control sequence" refers to nucleic acid sequences, such as initiator sequences, enhancer sequences, and promoter sequences, which induce, repress, or otherwise control the transcription of protein encoding nucleic acid sequences to which they are operably linked.

In still a further embodiment, a recombinant adeno-associated virus (AAV) vector is provided for delivery of the RDH12 constructs and optimized sequences described herein. The term "AAV" as used herein refers to the dozens of naturally occurring and available adeno-associated viruses, as well as artificial AAVs. An adeno-associated virus (AAV) viral vector is an AAV DNase-resistant particle having an AAV protein capsid into which is packaged nucleic acid sequences for delivery to target cells. An AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. AAVs may be selected as sources for capsids of AAV viral vectors as identified above. See, e.g., US Published Patent Application No. 2007-0036760-A1; US Published Patent Application No. 2009-0197338-A1; EP 1310571. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689, and WO 2003/042397 (rh.10). These documents also describe other AAV which may be selected for generating AAV and are incorporated by reference.

Among the AAVs isolated or engineered from human or non-human primates (NHP) and well characterized, human AAV2 is the first AAV that was developed as a gene transfer vector; it has been widely used for efficient gene transfer experiments in different target tissues and animal models. Unless otherwise specified, the AAV capsid, ITRs, and other selected AAV components described herein, may be readily selected from among any AAV, including, without limitation, the AAVs commonly identified as AAV1, AAV2, AAV3, AAV4, AAV5, AAV6, AAV7, AAV8, AAV9, AAV8 bp, AAV7M8 and AAVAnc80, variants of any of the known or mentioned AAVs or AAVs yet to be discovered or variants or mixtures thereof. See, e.g., WO 2005/033321, which is incorporated herein by reference.

In another embodiment, the AAV capsid is an AAV8 bp capsid, which preferentially targets bipolar cells. See, WO 2014/024282, which is incorporated herein by reference. In another embodiment, the AAV capsid is an AAV7m8 capsid, which has shown preferential delivery to the outer retina. See, Dalkara et al, In Vivo-Directed Evolution of a New Adeno-Associated Virus for Therapeutic Outer Retinal Gene Delivery from the Vitreous, Sci Transl Med 5, 189ra76 (2013), which is incorporated herein by reference. In one embodiment, the AAV capsid is an AAV8 capsid. In another embodiment, the AAV capsid an AAV9 capsid. In another embodiment, the AAV capsid an AAV5 capsid.

In some embodiments, an AAV capsid for use in the viral vector can be generated by mutagenesis (i.e., by insertions, deletions, or substitutions) of one of the aforementioned AAV capsids or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps. In one embodiment, it is desirable to utilize an AAV capsid which shows tropism for the desired target cell, e.g., photoreceptors, RPE or other ocular cells. In one embodiment, the AAV capsid is a tyrosine capsid-mutant in which certain surface exposed tyrosine residues are substituted with phenylalanine (F).

Such AAV variants are described, e.g., in Mowat et al, January 2014, Tyrosine capsid-mutant AAV vectors for gene delivery to the canine retina from a subretinal or intravitreal approach, Gene Therapy 21, 96-105, which is incorporated herein by reference. In one embodiment the capsid is an AAV8 capsid with a Y733F mutation. In another embodiment, the capsid is an AAV8 capsid with Y447F, Y733F and T494V mutations (also called "AAV8(C&G+T494V)" and "rep2-cap8(Y447F+733F+T494V)"), as described by Kay et al, April 2013, Targeting Photoreceptors via Intravitreal Delivery Using Novel, Capsid-Mutated AAV Vectors, PLoS One. 2013; 8(4): e62097, which is incorporated herein by reference.

As used herein, relating to AAV, the term "variant" means any AAV sequence which is derived from a known AAV sequence, including those sharing at least 70%, at least 75%, at least 80%, at least 85%, at least 90%, at least 95%, at least 97%, at least 99% or greater sequence identity over the amino acid or nucleic acid sequence. In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3). In one embodiment, the AAV capsid shares at least 95% identity with the AAV8 vp3. In another embodiment, a self-complementary AAV is used.

The ITRs or other AAV components may be readily isolated or engineered using techniques available to those of skill in the art from an AAV. Such AAV may be isolated, engineered, or obtained from academic, commercial, or public sources (e.g., the American Type Culture Collection, Manassas, Va.). Alternatively, the AAV sequences may be engineered through synthetic or other suitable means by reference to published sequences such as are available in the literature or in databases such as, e.g., GenBank, PubMed, or the like. AAV viruses may be engineered by conventional molecular biology techniques, making it possible to optimize these particles for cell specific delivery of nucleic acid sequences, for minimizing immunogenicity, for tuning stability and particle lifetime, for efficient degradation, for accurate delivery to the nucleus, etc.

As used herein, "artificial AAV" means, without limitation, an AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV, non-contiguous portions of the same AAV, from a non-AAV viral source, or from a non-viral source. An artificial AAV may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/5 and AAV2/8 are exemplary pseudotyped vectors.

For packaging an expression cassette or rAAV genome or production plasmid or proviral plasmid into virions, the ITRs are the only AAV components required in cis in the same construct as the transgene. In one embodiment, the coding sequences for the replication (rep) and/or capsid (cap) are removed from the AAV genome and supplied in trans or by a packaging cell line in order to generate the AAV vector. For example, as described above, a pseudotyped AAV may contain ITRs from a source which differs from the source of the AAV capsid. In one embodiment, AAV2/5 and AAV2/8 are exemplary pseudotyped vectors. Additionally or alternatively, a chimeric AAV capsid may be utilized. Still other AAV components may be selected. Sources of such AAV sequences are described herein and may also be isolated or engineered obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

"Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

In one embodiment, the AAV is a self-complementary AAV2/8. See, e.g., Buie et al, January 2010, Self-complementary AAV Virus (scAAV) Safe and Long-term Gene Transfer in the Trabecular Meshwork of Living Rats and Monkeys, Invest Ophthalmol Vis Sci., 51(1): 236-248, and Ryals et al, April 2011, Quantifying transduction efficiencies of unmodified and tyrosine capsid mutant AAV vectors in vitro using two ocular cell lines, Mol Vis.; 17:1090-102, which are incorporated herein by reference. In one embodiment, the AAV is a self-complementary AAV2/8 having at least a Y733F mutation. See, Ku et al, December 2011, Gene therapy using self-complementary Y733F capsid mutant AAV2/8 restores vision in a model of early onset Leber congenital amaurosis, Hum Mol Genet., 20(23): 4569-4581, which is incorporated herein by reference. In another embodiment, the AAV is a self-complementary AAV2/8 having at least Y447F+733F+T494V mutations. See, Kay et al, 2013, cited herein.

In one embodiment, the vectors useful in compositions and methods described herein contain, at a minimum, sequences encoding a selected AAV capsid, e.g., an AAV8 capsid, or a fragment thereof. In another embodiment, useful vectors contain, at a minimum, sequences encoding a selected AAV rep protein, e.g., AAV5 rep protein, or a fragment thereof. Optionally, such vectors may contain both AAV cap and rep proteins. In vectors in which both AAV rep and cap are provided, the AAV rep and AAV cap sequences can both be of one origin, e.g., all AAV5 origin or all AAV7 origin, etc.

Alternatively, vectors may be used in which the rep sequences are from an AAV which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV to form a chimeric AAV vector, such as AAV2/8 described in U.S. Pat. No. 7,282,199, which is incorporated by reference herein.

Certain compositions described herein are isolated, or synthetically or recombinantly engineered nucleic acid sequences that provide novel codon-optimized sequences encoding a functional RDH12. In one embodiment, the optimized nucleic acid sequences encoding the hRDH12 constructs described herein are engineered into any suitable genetic element, e.g., naked DNA, phage, transposon, cosmid, RNA molecule (e.g., mRNA), episome, etc., which transfers the RDH12 sequences carried thereon to a host cell, e.g., for generating nanoparticles carrying DNA or RNA, viral vectors in a packaging host cell and/or for delivery to a host cells in subject. In one embodiment, the genetic element is a plasmid.

The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

A variety of expression cassettes are provided which employ SEQ ID NO. 3 for expression of multiple or different versions of the hRDH12 protein. As used herein, an "expression cassette" refers to a nucleic acid molecule which comprises coding sequences for the optimized RDH12 proteins, promoter, and may include other regulatory sequences therefor, which cassette may be engineered into a genetic element or plasmid, and/or packaged into the capsid of a viral vector (e.g., a viral particle). In one embodiment, an expression cassette comprises a codon optimized nucleic acid sequence that encodes RDH12. In one embodiment, the cassette provides the codon optimized RDH12 operatively associated with expression control sequences that direct expression of the codon optimized nucleic acid sequence that encodes RDH12 in a host cell.

In another embodiment, an expression cassette comprises a codon optimized nucleic acid sequence that encodes RDH12. In one embodiment, the cassette provides the codon optimized RDH12 operatively associated with expression control sequences that direct expression of the codon optimized nucleic acid sequence that encodes RDH12 in a host cell.

In still another embodiment, an expression cassette comprises a codon optimized nucleic acid sequence that encodes a functional, optimized RDH12. In one embodiment of such an expression cassette, the sequence encoding RDH12 is operatively associated with the a first expression control sequence(s) that direct expression of a naturally occurring nucleic acid sequence that encodes RDH12 in a host cell. As described above for the expression cassettes containing RDH12, in embodiments which express multiple copies or multiple different versions of functional RDH12, the codon optimized sequence may be positioned, 5' or 3' to another version of the sequences. One of skill in the art may readily design constructs for expression of multiple copies of RDH12 in view of the teachings of this specification and the prior art.

As described herein, an expression cassette can be flanked on its 5' end by a 5'AAV inverted terminal repeat sequence (ITR) and on its 3' end by a 3' AAV ITR. Thus, this rAAV ITR-flanked expression cassette contains the minimal sequences required to package the expression cassette into an AAV viral particle, i.e., the AAV 5' and 3' ITRs. The AAV ITRs may be obtained from the ITR sequences of any AAV, such as described herein. These ITRs may be of the same AAV origin as the capsid employed in the resulting recombinant AAV, or of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Each rAAV genome can be then introduced into a proviral plasmid following the teachings of WO2012/158757. The proviral plasmids are cultured in the host cells which express the AAV cap and/or rep proteins. In the host cells, each rAAV genome is rescued and packaged into the capsid protein or envelope protein to form an infectious viral particle.

In yet another embodiment, a vector comprising any of the expression cassettes described herein is provided. As described above, such vectors can be plasmids of variety of origins and are useful in certain embodiments for the generation of recombinant replication defective viruses as described further herein.

In one another embodiment, the vector is a proviral plasmid that comprises an AAV capsid and an recombinant AAV-ITR flanked expression cassette, wherein said cassette comprises a codon optimized nucleic acid sequence that encodes RDH12 or multiple (i.e., at least two) copies of RDH12, and expression control sequences that direct expression of the encoded protein in a host cell.

One type of proviral plasmid comprises a modular recombinant expression cassette that permits portions of the components of cassette to be removed and repeatedly replaced with other components without destroying the restriction sites in the plasmid. Such a proviral plasmid is one that contains a 5' AAV ITR sequence, the ITR flanked upstream by restriction site 1 and downstream by restriction site 2; a selected promoter flanked upstream by restriction site 2 and downstream by restriction site 3. Another component of the modular rAAV is a polylinker sequence comprising at least restriction site 3, restriction site 4 and restriction site 5, that contains a codon optimized nucleic acid sequence that encodes RDH12, or two or more copies of a sequence that encodes RDH12, at least one such sequence being a codon optimized nucleic acid sequence encoding RDH12. The RDH12 encoding sequences are located between any two of the restriction sites 3, 4 and 5, and are operatively linked to, and under the regulatory control of, the promoter. Alternatively, the second encoding sequence is inserted into the polylinker sequence along with the second expression control sequence of the expression cassette as described above.

Additional components of the modular rAAV cassette include a polyadenylation sequence flanked upstream by restriction site 4 or 5 and downstream by restriction site 6; and a 3' AAV ITR sequence flanked upstream by restriction site 6 and downstream by restriction site 7. The proviral plasmid also contains elements necessary for replication in bacterial cells, and a resistance gene. Each of the above-noted restriction sites 1 through 7 occurs only once in the proviral plasmid and is cleaved by a different enzyme that cannot cleave another restriction site in the plasmid and thereby permit independent and repeated removal, replacement or substitution of the entire rAAV modular cassette or only the elements flanked by those restriction sites from the plasmid. Such plasmids are described in detail in International Patent Application Publication No. WO2012/158757, incorporated by reference herein.

A suitable recombinant adeno-associated virus (AAV) is generated by culturing a host cell which contains a nucleic acid sequence encoding an adeno-associated virus (AAV) serotype capsid protein, or fragment thereof, as defined herein; a functional rep gene; a minigene composed of, at a minimum, AAV inverted terminal repeats (ITRs) and a NPHP5 nucleic acid sequence; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

Most suitably, such a stable host cell will contain the required component(s) under the control of an inducible promoter. However, the required component(s) may be under the control of a constitutive promoter. Examples of suitable inducible and constitutive promoters are provided herein, in the discussion below of regulatory elements suitable for use with the transgene, i.e., RDH12. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfers the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, 1993 *J. Virol.*, 70:520-532 and U.S. Pat. No. 5,478,745, among others. These publications are incorporated by reference herein.

The minigene is composed of, at a minimum, a RDH12 nucleic acid sequence (the transgene), as described above, and its regulatory sequences, and 5' and 3' AAV inverted terminal repeats (ITRs). In one desirable embodiment, the ITRs of AAV serotype 2 are used. However, ITRs from other suitable serotypes may be selected. It is this minigene which is packaged into a capsid protein and delivered to a selected host cell.

The regulatory sequences include conventional control elements which are operably linked to the RDH12 gene in a manner which permits its transcription, translation and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters, are known in the art and may be utilized.

The regulatory sequences useful in the constructs of the present invention may also contain an intron, desirably located between the promoter/enhancer sequence and the gene. One desirable intron sequence is derived from SV-40, and is a 100 bp mini-intron splice donor/splice acceptor referred to as SD-SA. Another suitable sequence includes the woodchuck hepatitis virus post-transcriptional element. (See, e.g., L. Wang and I. Verma, 1999 Proc. Natl. Acad. Sci., USA, 96:3906-3910). PolyA signals may be derived from many suitable species, including, without limitation SV-40, human and bovine.

Another regulatory component of the rAAV useful in the method of the invention is an internal ribosome entry site (IRES). An IRES sequence, or other suitable system, may be used to produce more than one polypeptide from a single gene transcript. An IRES (or other suitable sequence) is used to produce a protein that contains more than one polypeptide chain or to express two different proteins from or within the same cell. An exemplary IRES is the poliovirus internal ribosome entry sequence, which supports transgene expression in photoreceptors, RPE and ganglion cells. Preferably, the IRES is located 3' to the transgene in the rAAV vector.

The selection of the promoter to be employed in the rAAV may be made from among a wide number of constitutive or inducible promoters that can express the selected transgene in the desired an ocular cell. In another embodiment, the promoter is cell-specific. The term "cell-specific" means that the particular promoter selected for the recombinant vector can direct expression of the selected transgene in a particular ocular cell type. In one embodiment, the promoter is specific for expression of the transgene in photoreceptor cells. In another embodiment, the promoter is specific for expression in the rods and cones. In another embodiment, the promoter is specific for expression in the rods. In another embodiment, the promoter is specific for expression in the cones. In another embodiment, the promoter is specific for expression of the transgene in RPE cells. In another embodiment, the transgene is expressed in any of the above noted ocular cells.

The promoter may be derived from any species. Exemplary promoters may be the human G-protein-coupled receptor protein kinase 1 (GRK1) promoter (Genbank Accession number AY327580). In another embodiment, the promoter is a 292 nt fragment (positions 1793-2087) of the GRK1 promoter (See, Beltran et al, Gene Therapy 2010 17:1162-74, which is hereby incorporated by reference herein). In another preferred embodiment, the promoter is the human interphotoreceptor retinoid-binding protein proximal (IRBP) promoter. In one embodiment, the promoter is a 235 nt fragment of the hIRBP promoter.

In another embodiment, promoter is the native promoter for the gene to be expressed. In one embodiment, the promoter is the RDH12 proximal promoter. Other promoters useful in the invention include, without limitation, the RPGR proximal promoter (Shu et al, IOVS, May 2102), the rod opsin promoter, the red-green opsin promoter, the blue opsin promoter, the cGMP-β-phosphodiesterase promoter, the mouse opsin promoter (Beltran et al 2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); beta phosphodiesterase (PDE) promoter; the retinitis pigmentosa (RP1) promoter (Nicord et al, J. Gene Med, December 2007, 9(12):1015-23); the NXNL2/NXNL1 promoter (Lambard et al, PLoS One, October 2010, 5(10):e13025), the RPE65 promoter; the retinal degeneration slow/peripherin 2 (Rds/perph2) promoter (Cai et al, Exp Eye Res. 2010 August; 91(2):186-94); and the VMD2 promoter (Kachi et al, Human Gene Therapy, 2009 (20:31-9)). Each of these documents is incorporated by reference herein. In another embodiment, the promoter is selected from human EF1α promoter, rhodopsin promoter, rhodopsin kinase, interphotoreceptor binding protein (IRBP), cone opsin promoters (red-green, blue), cone opsin upstream sequences containing the red-green cone locus control region, cone transducing, and transcription factor promoters (neural retina leucine zipper (Nrl) and photoreceptor-specific nuclear receptor Nr2e3, bZIP).

In one embodiment, the promoter is of a small size, under 1000 bp, due to the size limitations of the AAV vector. In another embodiment, the promoter is under 400 bp. Other promoters may be selected by one of skill in the art.

In another embodiment, the promoter is a ubiquitous or constitutive promoter. An example of a suitable promoter is a hybrid chicken β-actin (CBA) promoter with cytomegalovirus (CMV) enhancer elements. In another embodiment, the promoter is the CB7 promoter. Other suitable promoters include the human β-actin promoter, the human elongation factor-1α promoter, the cytomegalovirus (CMV) promoter, the simian virus 40 promoter, and the herpes simplex virus thymidine kinase promoter. See, e.g., Damdindorj et al, (August 2014) A Comparative Analysis of Constitutive Promoters Located in Adeno-Associated Viral Vectors. PLoS ONE 9(8): e106472. Still other suitable promoters include viral promoters, constitutive promoters, regulatable promoters [see, e.g., WO 2011/126808 and WO 2013/04943]. Alternatively a promoter responsive to physiologic cues may be utilized in the expression cassette, rAAV genomes, vectors, plasmids and viruses described herein. In one embodiment, the promoter is of a small size, under 1000 bp, due to the size limitations of the AAV vector. In another embodiment, the promoter is under 400 bp. Other promoters may be selected by one of skill in the art.

Examples of constitutive promoters useful in the invention include, without limitation, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the chicken β-actin (CBA) promoter, the phosphoglycerol kinase (PGK) promoter, the EF1 promoter (Invitrogen), and the immediate early CMV enhancer coupled with the CBA promoter (Beltran et al, Gene Therapy 2010 cited above).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system; the ecdysone insect promoter, the tetracycline-repressible system, the tetracycline-inducible system, the RU486-inducible system and the rapamycin-inducible system. Other types of inducible promoters which may be useful in this context are those which are regulated by a specific physiological state, e.g., temperature, acute phase, a particular differentiation state of the cell, or in replicating cells only. Any type of inducible promoter which is tightly regulated and is specific for the particular target ocular cell type may be used.

In other embodiments, the cassette, vector, plasmid and virus constructs described herein contain other appropriate transcription initiation, termination, enhancer sequences, efficient RNA processing signals such as splicing and polyadenylation (polyA) signals; TATA sequences; sequences that stabilize cytoplasmic mRNA; sequences that enhance translation efficiency (i.e., Kozak consensus sequence); introns; sequences that enhance protein stability; and when desired, sequences that enhance secretion of the encoded product. The expression cassette or vector may contain none, one or more of any of the elements described herein. Examples of suitable polyA sequences include, e.g., SV40, bovine growth hormone (bGH), and TK polyA. Examples of suitable enhancers include, e.g., the CMV enhancer, the RSV enhancer, the alpha fetoprotein enhancer, the TTR minimal promoter/enhancer, LSP (TH-binding globulin promoter/alpha1-microglobulin/bikunin enhancer), amongst others.

Other enhancer sequences useful in the invention include the IRBP enhancer (Nicord 2007, cited above), immediate early cytomegalovirus enhancer, one derived from an immunoglobulin gene or SV40 enhancer, the cis-acting element identified in the mouse proximal promoter, etc.

Selection of these and other common vector and regulatory elements are conventional and many such sequences are available. See, e.g., Sambrook et al, and references cited therein at, for example, pages 3.18-3.26 and 16.17-16.27 and Ausubel et al., Current Protocols in Molecular Biology, John Wiley & Sons, New York, 1989). Of course, not all vectors and expression control sequences will function equally well to express all of the transgenes of this invention. However, one of skill in the art may make a selection among these, and other, expression control sequences without departing from the scope of this invention.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level.

In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety.

The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, N.Y. (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

In other embodiments, the cassette, vector, plasmid and virus constructs described herein contain other appropriate transcription initiation, termination, enhancer sequences, efficient RNA processing signals such as splicing and polyadenylation (polyA) signals; TATA sequences; sequences that stabilize cytoplasmic mRNA; sequences that enhance translation efficiency (i.e., Kozak consensus sequence); introns; sequences that enhance protein stability; and when desired, sequences that enhance secretion of the encoded product. The expression cassette or vector may contain none, one or more of any of the elements described herein. Examples of suitable polyA sequences include, e.g., SV40, bovine growth hormone (bGH), and TK polyA. Examples of suitable enhancers include, e.g., the CMV enhancer, the RSV enhancer, the alpha fetoprotein enhancer, the TTR minimal promoter/enhancer, LSP (TH-binding globulin promoter/alpha1-microglobulin/bikunin enhancer), amongst others.

Thus, in one embodiment novel AAV proviral plasmids carrying native or optimized cDNAs of Retinal Dehydrogenase 12 (RDH12) that encode normal or functional RDH12 protein, such plasmids are capable of being packaged in the AAV vectors. These vectors have demonstrated biological activities both in vitro and in vivo.

In one embodiment, a method of generating a recombinant rAAV comprises obtaining a plasmid containing a rAAV genome as described above and culturing a packaging cell carrying the plasmid in the presence of sufficient viral sequences to permit packaging of the AAV viral genome into an infectious AAV envelope or capsid. Specific methods of rAAV vector generation are described above and may be employed in generating a rAAV vector that can deliver one or more of the codon optimized RDH12 or RDH12 in the expression cassettes and genomes described above and in the examples below.

In still another aspect, a method of gene editing is employed to correct a mutation or undesirable RDH12 gene sequence in the eye. One desirable method of gene editing employs the "CRISPR/Cas9" system. CRISPR/Cas is a technique which has been described as having potential in correction of diseases associated with a genetic mutation or a specific phenotype. The Clustered Regularly Interspaced Short Palindromic Repeats (CRISPR) and CRISPR-associated protein (Cas9) system has two distinct components: (1) a guide RNA and (2) an endonuclease, in this case the CRISPR associated (Cas) nuclease, Cas9. The guide RNA is a combination of endogenous bacterial crRNA (CRISPR RNA) and tracrRNA (transactivating crRNA) into a single chimeric guide RNA (gRNA) transcript. The gRNA combines the targeting specificity of crRNA with the scaffolding properties of tracrRNA into a single transcript. When the gRNA and the Cas9 are expressed in the cell, the genomic target sequence can be modified or permanently disrupted. This system has been employed for genomic engineering for mammalian systems, see, e.g., Cong, L., et al. 2013. Science 339: 819-823; Mali, P., et al. 2013 Science 339: 823-826; Ran, F. A., et al. 2013. Nat. Protoc. 8: 2281-2308; and Shalem, O., et al. 2014 Science 343: 84-87. The CRISPR Type II system is currently the most commonly used RNA-guided endonuclease technology for genome engineering. Adeno-associated viruses have been described as being useful vectors for gene therapy involving the CRISPR-Cas system. See, e.g., Yin et al, 2014 Biotechnology, 32: 551-3 and 2015 Nature Biotechnology, 33: 102-6.

In still another embodiment, these gene editing techniques can be employed on selected cells to insert the RDH12-encoding sequence (native or codon-optimized). Such cells can include HEPG2 cells or induced pluripotent stem cells (iPSCs), which can then be used as models to examine the functions of the vectors, recombinant viruses, and other compositions and reagents herein.

In yet other aspects, these nucleic acid sequences, vectors, proviral plasmids, expression cassettes, rAAV-ITR flanked expression cassettes, viral vectors, including rAAV viral vectors are useful in pharmaceutical compositions, which also comprise a pharmaceutically acceptable carrier. Such pharmaceutical compositions are used to express the optimized RDH12 or multiple copies of RDH12 in the ocular cells through delivery by such recombinantly engineered AAVs or artificial AAV's.

To prepare these ophthalmic pharmaceutical compositions containing the nucleic acid sequences, vectors, rAAV genomes and rAAV viral vectors, the sequences or vectors or viral vector are preferably assessed for contamination by conventional methods and then formulated into a pharmaceutical composition suitable for administration to the eye. In general, ophthalmic pharmaceutical preparations are sterile formulations essentially free from foreign particles, suitably compounded and packaged for instillation in to the eye. In one embodiment, the formulation is suitable for subretinal injection. Such formulation involves the use of a pharmaceutically and/or physiologically acceptable vehicle or carrier, particularly one suitable for administration to the eye. Suitable pharmaceutical carriers including phosphate buffered saline solutions, water, emulsions, such as oil/water emulsions or microemulsions, suspensions, various types of wetting agents, sterile solutions, in liposomes, in niosomes, discomes, or even in ointment or gels, such as buffered saline or other buffers, e.g., HEPES, to maintain pH at appropriate physiological levels.

Optionally, other medicinal agents, such as pharmaceutical agents, stabilizing agents, buffers, adjuvants, diluents, or surfactants, etc. are included. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes Tween. If the virus is to be stored long-term, it may be frozen in the presence of glycerol or Tween20.

In one embodiment, the contents of the formulation are designed to maintain a pH range of 4.75 to 7.40. Topical products also require adjustment of tonicity close to that of natural tears. Generally, a range of 0.5% to 2% saline tonicity is well-tolerated. Suitable surfactants also include, for example, synthetic surfactants, such as colfosceril palmitate (Exosurf), a mixture of DPPC with hexadecanol and tyloxapol added as spreading agents; Pumactant, a mixture of DPPC and PG; KL-4 which is composed of DPPC, palmitoyl-oleoyl phosphatidylglycerol, and palmitic acid, combined with a 21 amino acid synthetic peptide that mimics the structural characteristics of SP-B; Venticute, a combination of DPPC, PG, palmitic acid and recombinant SP-C; or animal derived surfactants such as Beractant (Alveofact or Survanta), Calfactant (Infasurf) or Poractant alfa (Curosurf). Another useful surfactant is Surfaxin (an FDA approved synthetic peptide. Still another useful surfactant is Pluronic F68.

In one exemplary specific embodiment, a suitable formulation contains 180 mM NaCl, 10 mM sodium phosphate buffer (NaPi), pH 7.3 with 0.0001%-0.01% Pluronic F68 (PF68) surfactant. The exact composition of the saline component of the buffer ranges from 160 mM to 180 mM NaCl. Optionally a different pH buffer (potentially HEPEs, sodium bicarbonate, or TRIS) is used in place of the buffer specifically described. Still alternatively, a buffer containing 0.9% NaCl is useful.

Optionally, the compositions of the invention may contain, in addition to the rAAV and/or variants and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The pharmaceutical compositions containing a replication-defective rAAV viruses can be formulated with a physiologically acceptable carrier for use in gene transfer and gene therapy applications. In the case of AAV viral vectors, quantification of the genome copies ("GC"), vector genomes, or virus particles may be used as the measure of the dose contained in the formulation or suspension. Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal). In another method the effective dose of a recombinant adeno-associated virus carrying a nucleic acid sequence encoding the optimized RDH12 transgene under the desirably are measured as described in S. K. McLaughlin et al, 1988 J. Virol., 62:1963. In another method, the titer is determined using droplet digital PCR (ddPCR). See, Lock as described in, e.g., M. Lock et al, Hu Gene Therapy Methods, 2014 April; 25(2):115-25. doi: 10.1089/hgtb.2013.131. Epub 2014 Feb. 14, which is incorporated herein by reference.

By "administering" as used in the methods means delivering the composition to the target selected cell which is characterized by the ocular disease. In one embodiment, the method involves delivering the composition by subretinal injection to the photoreceptor cells or other ocular cells. In another embodiment, intravitreal injection to ocular cells is employed. In still another method, injection via the palpebral vein to ocular cells may be employed. Still other methods of administration may be selected by one of skill in the art given this disclosure. By "administering" or "route of administration" is delivery of composition described herein, with or without a pharmaceutical carrier or excipient, of the subject. Routes of administration may be combined, if desired. In some embodiments, the administration is repeated periodically. The pharmaceutical compositions described herein are designed for delivery to subjects in need thereof by any suitable route or a combination of different routes. Direct delivery to the eye (optionally via ocular delivery, intra-retinal injection, intravitreal, topical), or delivery via systemic routes, e.g., intraarterial, intraocular, intravenous, intramuscular, subcutaneous, intradermal, and other parental routes of administration. The nucleic acid molecules and/or vectors described herein may be delivered in a single composition or multiple compositions. Optionally, two or more different AAV may be delivered, or multiple viruses [see, e.g., WO20 2011/126808 and WO 2013/049493]. In another embodiment, multiple viruses may contain different replication-defective viruses (e.g., AAV and adenovirus), alone or in combination with proteins.

As used herein, the term "treatment" or "treating" is defined encompassing administering to a subject one or more compounds or compositions described herein for the purposes of amelioration of one or more symptoms of an ocular disease. "Treatment" can thus include one or more of reducing onset or progression of an ocular disease, preventing disease, reducing the severity of the disease symptoms, or retarding their progression, including the progression of blindness, removing the disease symptoms, delaying onset of disease or monitoring progression of disease or efficacy of therapy in a given subject.

As used herein, the term "dosage" can refer to the total dosage delivered to the subject in the course of treatment, or the amount delivered in a single unit (or multiple unit or split dosage) administration. The pharmaceutical virus compositions can be formulated in dosage units to contain an amount of replication-defective virus carrying the nucleic acid sequences encoding RDH12 as described herein. Dosages can be expressed in genome copies (GC) of the nucleic acid sequences. Dosages can also be expressed in terms of viral particles. In one embodiment, a suitable dosage is in the range of about $1.0\times10^6$ GC or viral particles to about $1.0\times10^{15}$ GC including all integers or fractional amounts within the range. In one embodiment, the compositions are formulated to contain, or dosages administered in amounts of, at least $1\times10^6$, $2\times10^6$, $3\times10^6$, $4\times10^6$, $5\times10^6$, $6\times10^6$, $7\times10^6$, $8\times10^6$, or $9\times10^6$ GC per dose including all integers or fractional amounts within the range. In one embodiment, the compositions are formulated to contain, or dosages administered in amounts of, at least $1\times10^7$, $2\times10^7$, $3\times10^7$, $4\times10^7$, $5\times10^7$, $6\times10^7$, $7\times10^7$, $8\times10^7$, or $9\times10^7$ GC per dose including all integers or fractional amounts within the range. In one embodiment, the compositions are formulated to contain at least $1\times10^8$, $2\times10^8$, $3\times10^8$, $4\times10^8$, $5\times10^8$, $6\times10^8$, $7\times10^8$, $8\times10^8$, or $9\times10^8$ GC per dose including all integers or fractional amounts within the range. In one embodiment, the compositions are formulated to contain at least $1\times10^9$, $2\times10^9$, $3\times10^9$, $4\times10^9$, $5\times10^9$, $6\times10^9$, $7\times10^9$, $8\times10^9$, or $9\times10^9$ GC per dose including all integers or fractional amounts within the range. In another embodiment, the compositions are formulated to contain at least $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ GC per dose including all integers or fractional amounts within the range. In another embodiment, the compositions are formulated to contain at least $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ GC per dose including all integers or fractional amounts within the range. In another embodiment, the compositions are formulated to contain at least $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ GC per dose including all integers or fractional amounts within the range. In another embodiment, the compositions are formulated to contain at least $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ GC per dose including all integers or fractional amounts within the range. In another embodiment, the compositions are formulated to contain at least $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ GC per dose including all integers or fractional amounts within the range. In another embodiment, the compositions are formulated to contain at least $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per dose including all integers or fractional amounts within the range. In one embodiment, for human application the dose can range from $1\times10^6$ to about $1\times10^{13}$ GC per dose including all integers or fractional amounts within the range. In one embodiment, for human application the dose can range from $1\times10^{10}$ to about $1\times10^{12}$ GC per dose including all integers or fractional amounts within the range. Still other doses and dosages may be determined by the attending physician.

These above doses may be administered in a variety of volumes of carrier, excipient or buffer formulation, ranging from about 25 to about 1000 microliters, including all numbers within the range, depending on the size of the area to be treated, the viral titer used, the route of administration, and the desired effect of the method. In one embodiment, the volume of carrier, excipient or buffer is at least about 25 μl. In one embodiment, the volume is about 50 μl. In another embodiment, the volume is about 75 μl. In another embodiment, the volume is about 100 μl. In another embodiment, the volume is about 125 μl. In another embodiment, the volume is about 150 μl. In another embodiment, the volume is about 175 μl. In yet another embodiment, the volume is about 200 μL. In another embodiment, the volume is about 225 μl. In yet another embodiment, the volume is about 250 μl. In yet another embodiment, the volume is about 275 μl. In yet another embodiment, the volume is about 300 μL. In yet another embodiment, the volume is about 325 μL. In another embodiment, the volume is about 350 μl. In another embodiment, the volume is about 375 μl. In another embodiment, the volume is about 400 μl. In another embodiment, the volume is about 450 n another embodiment, the volume is about 500 μl. In another embodiment, the volume is about 550 μl. In another embodiment, the volume is about 600 μl. In another embodiment, the volume is about 650 μl. In another embodiment, the volume is about 700 μl. In another embodiment, the volume is between about 700 and 1000 μl.

In one embodiment, the viral constructs may be delivered in concentrations of from at least $1\times10^6$ to about least $1\times10^{11}$ GCs in volumes of about 1 µl to about 3 µl for small animal subjects, such as mice. For larger veterinary subjects having eyes about the same size as human eyes, the larger human dosages and volumes stated above, e.g., $1\times10^6$ to about $1\times10^{15}$ GC per dose, are useful. See, e.g., Diehl et al, J. Applied Toxicology, 21:15-23 (2001) for a discussion of good practices for administration of substances to various veterinary animals. This document is incorporated herein by reference.

It is desirable that the lowest effective concentration of virus or other delivery vehicle be utilized in order to reduce the risk of undesirable effects, such as toxicity, retinal dysplasia and detachment. In one embodiment, if the codon optimized sequences are more effective than naturally-occurring sequences in humans, it is anticipated that lower dosages stated above will be useful. Still other dosages in these ranges may be selected by the attending physician, taking into account the physical state of the subject, preferably human, being treated, the age of the subject, the particular ocular disorder (e.g., RDH12-mediated disorder) and the degree to which the disorder, if progressive, has developed.

Yet another aspect described herein are various methods of treating an RDH12-mediated disorder or ocular disorder by administering the codon optimized RDH12 DNA, vectors, viruses or other pharmaceutical compositions containing same. In another embodiment a method of preventing, treating, arresting progression of or ameliorating vision loss due to the above-described ocular diseases and retinal changes associated therewith is provided. Still other methods are designed for restoring partial or full vision or visual acuity to a subject with an ocular disorder. Vision loss associated with LCA or RP refers to any decrease in peripheral vision, central (reading) vision, night vision, day vision, loss of color perception, loss of contrast sensitivity, or reduction in visual acuity. Other vision problems that may be treated using the described methods include photophobia and nystagmus.

Generally, the methods include administering to a mammalian subject in need thereof, an effective amount of a composition comprising a recombinant adeno-associated virus (AAV) carrying a nucleic acid sequence encoding a normal or functional RDH12 protein, or fragment thereof, under the control of regulatory sequences which express the product of the gene in the subject's ocular cells, and a pharmaceutically acceptable carrier.

In one embodiment, such a method is designed for treating, retarding or halting progression of blindness in a mammalian subject having one or more of the ocular diseases described above, such as LCA or RP. The rAAV carrying the RDH12 optimized coding sequence or another functional RDH12 sequence, preferably suspended in a physiologically compatible carrier, diluent, excipient and/or adjuvant, may be administered to a desired subject including without limitation, a cat, dog, or other non-human mammalian subject. This method comprises administering to a subject in need thereof any of the nucleic acid sequences, expression cassettes, rAAV genomes, plasmids, vectors or rAAV vectors or compositions containing them. In one embodiment, the composition is delivered subretinally. In another embodiment, the composition is delivered intravitreally. In still another embodiment, the composition is delivered using a combination of administrative routes suitable for treatment of ocular diseases, and may also involve administration via the palpebral vein or other intravenous or conventional administration routes.

For use in these methods, the volume and viral titer of each dosage is determined individually, as further described herein, and may be the same or different from other treatments performed in the same, or contralateral, eye. In another embodiment, a single, larger volume treatment is made in order to treat the entire eye. The dosages, administrations and regimens may be determined by the attending physician given the teachings of this specification.

In one embodiment, the composition is administered in a single dosage selected from those above listed in a single affected eye. In another embodiment, the composition is administered as a single dosage selected from those above listed in a both affected eyes, either simultaneously or sequentially. Sequential administration may imply a time gap of administration from one eye to another from intervals of minutes, hours, days, weeks or months. In another embodiment, the method involves administering the compositions to an eye two or more dosages (e.g., split dosages).

In still other embodiments, the compositions described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

In certain embodiments of the invention it is desirable to perform non-invasive retinal imaging and functional studies to identify areas of the rod and cone photoreceptors to be targeted for therapy. In these embodiments, clinical diagnostic tests are employed to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc, depending upon the species of the subject being treated, their physical status and health and the dosage. In view of the imaging and functional studies, in some embodiments of the invention one or more injections are performed in the same eye in order to target different areas of the affected eye. The volume and viral titer of each injection is determined individually, as further described below, and may be the same or different from other injections performed in the same, or contralateral, eye. In another embodiment, a single, larger volume injection is made in order to treat the entire eye. In one embodiment, the volume and concentration of the rAAV composition is selected so that only the region of damaged rod and cone receptors is impacted. In another embodiment, the volume and/or concentration of the rAAV composition is a greater amount, in order reach larger portions of the eye, including non-damaged photoreceptors.

In one embodiment of the methods described herein, a one-time intra-ocular delivery of a composition such as those described herein, e.g., an AAV delivery of an optimized RDH12 cassette, is useful in preventing vision loss and blindness in millions of individuals affected with such ocular disorders or multi-systemic diseases without regard to genotype or environmental exposure.

Thus, in one embodiment, the composition is administered before disease onset. In another embodiment, the composition is administered prior to the initiation of vision impairment or loss. In another embodiment, the composition is administered after initiation of vision impairment or loss.

In yet another embodiment, the composition is administered when less than 90% of the rod and/or cones or photoreceptors are functioning or remaining, as compared to a non-diseased eye.

In another embodiment, the method includes performing additional studies, e.g., functional and imaging studies to determine the efficacy of the treatment. For examination in animals, such tests include retinal and visual function assessment via electroretinograms (ERGs) looking at rod and cone photoreceptor function, optokinetic nystagmus, pupillometry, water maze testing, light-dark preference histology (retinal thickness, rows of nuclei in the outer nuclear layer, immunofluorescence to document transgene expression, cone photoreceptor counting, staining of retinal sections with peanut agglutinin—which identifies cone photoreceptor sheaths). Other suitable tests of efficacy are sampling of anterior chamber fluid to document presence of the RDH12 transgenic proteins.

Specifically for human subjects, following administration of a dosage of a compositions described in this specification, the subject is tested for efficacy of treatment using electroretinograms (ERGs) to examine rod and cone photoreceptor function, pupillometry visual acuity, contrast sensitivity color vision testing, visual field testing (Humphrey visual fields/Goldmann visual fields), perimetry mobility test (obstacle course), and reading speed test. Other useful post-treatment efficacy test to which the subject is exposed following treatment with a pharmaceutical composition described herein are functional magnetic resonance imaging (fMRI), full-field light sensitivity testing, retinal structure studies including optical coherence tomography, fundus photography, fundus autofluorescence, adaptive optics scanning, and/or laser ophthalmoscopy. These and other efficacy tests are described in U.S. Pat. No. 8,147,823; in co-pending International patent application publication WO 2014/011210 or WO 2014/124282, incorporated by reference.

In yet another embodiment, any of the above described methods is performed in combination with another, or secondary, therapy. In still other embodiments, the methods of treatment of these ocular diseases involve treating the subject with the composition described in detail herein in combination with another therapy, such as antibiotic treatment, palliative treatment for pain, and the like. The additional therapy may be any now known, or as yet unknown, therapy which helps prevent, arrest or ameliorate these mutations or defects or any of the effects associated therewith. The secondary therapy can be administered before, concurrent with, or after administration of the compositions described above. In one embodiment, a secondary therapy involves non-specific approaches for maintaining the health of the retinal cells, such as administration of neurotrophic factors, anti-oxidants, anti-apoptotic agents. The non-specific approaches are achieved through injection of proteins, recombinant DNA, recombinant viral vectors, stem cells, fetal tissue, or genetically modified cells. The latter could include genetically modified cells that are encapsulated.

In another embodiment, the invention provides a method to prevent, or arrest photoreceptor function loss, or increase photoreceptor function in the subject. Photoreceptor function may be assessed using the functional studies described above and in the examples below, e.g., ERG or perimetry, which are conventional in the art. As used herein "photoreceptor function loss" means a decrease in photoreceptor function as compared to a normal, non-diseased eye or the same eye at an earlier time point. As used herein, "increase photoreceptor function" means to improve the function of the photoreceptors or increase the number or percentage of functional photoreceptors as compared to a diseased eye (having the same ocular disease), the same eye at an earlier time point, a non-treated portion of the same eye, or the contralateral eye of the same patient.

In another aspect, the invention provides method of improving photoreceptor structure in the subject. As used herein "improving photoreceptor structure" refers (in the region of the retina that is treated) to one or more of an increase or decrease in outer nuclear layer (ONL) thickness, or arresting progression of ONL thickening or thinning, across the entire retina, in the central retina, or the periphery; increase or decrease in outer plexiform layer (OPL) thickness, or arresting progression of OPL thickening or thinning, across the entire retina, in the central retina, or the periphery; decrease in rod and cone inner segment (IS) shortening; decrease in shortening and loss of outer segments (OS); decrease in bipolar cell dendrite retraction, or an increase in bipolar cell dendrite length or amount; and reversal of opsin mislocalization.

In another aspect, the invention provides a method of preventing RDH12-associated-LCA in a subject at risk of developing said disease. Subjects at risk of developing this ocular disorder include those with a family history of LCA and those with one or more confirmed mutations in the RDH12 gene.

For each of the described methods, the treatment may be used to prevent the occurrence of retinal damage or to rescue eyes having mild or advanced disease. As used herein, the term "rescue" means to prevent progression of the disease to total blindness, prevent spread of damage to uninjured photoreceptor cells or to improve damage in injured photoreceptor cells. Thus, in one embodiment, the composition is administered before disease onset. In another embodiment, the composition is administered after the initiation of opsin mislocalization. In another embodiment, the composition is administered prior to the initiation of photoreceptor loss. In another embodiment, the composition is administered after initiation of photoreceptor loss. In yet another embodiment, the composition is administered when less than 90% of the photoreceptors are functioning or remaining, as compared to a non-diseased eye. In another embodiment, the composition is administered when less than 80% of the photoreceptors are functioning or remaining. In another embodiment, the composition is administered when less than 70% of the photoreceptors are functioning or remaining. In another embodiment, the composition is administered when less than 60% of the photoreceptors are functioning or remaining. In another embodiment, the composition is administered when less than 50% of the photoreceptors are functioning or remaining. In another embodiment, the composition is administered when less than 40% of the photoreceptors are functioning or remaining. In another embodiment, the composition is administered when less than 30% of the photoreceptors are functioning or remaining. In another embodiment, the composition is administered when less than 20% of the photoreceptors are functioning or remaining. In another embodiment, the composition is administered when less than 10% of the photoreceptors are functioning or remaining. In one embodiment, the composition is administered only to one or more regions of the eye, e.g., those which have retained photoreceptors. In another embodiment, the composition is administered to the entire eye.

In another embodiment, a method of treating or preventing RDH12-associated LCA or RP in a subject in need thereof is provided. The method includes identifying a subject having, or at risk of developing, RDH12-associated LCA or RP; performing genotypic analysis and identifying at least one mutation in the RHD12 gene; performing non-invasive retinal imaging and functional studies and identifying areas of retained photoreceptors to be targeted for therapy; and administering to the subject an effective concentration of a composition, whereby RDH12-associated LCA or RP is prevented, arrested or ameliorated. The composition includes a recombinant virus carrying a nucleic acid sequence encoding a normal photoreceptor cell-specific gene under the control of a promoter sequence which expresses the product of the gene in the photoreceptor cells, and a pharmaceutically acceptable carrier. Genotypic analysis is routine in the art and may include the use of PCR to identify one or more mutations in the nucleic acid sequence of the RDH12 gene. See, e.g., Meindl et al, Nat Gen, May 1996, 13:35, Vervoort, R. et al, 2000. Nat Genet 25(4): 462-466 (cited above); and Vervoort, R. and Wright, A. F. 2002. Human Mutation 19: 486-500, each of which is incorporated herein by reference.

The following examples disclose specific embodiments of the nucleic acid sequences, expression cassettes, rAAV genome and viral vectors for use in treating the ocular diseases specified herein. These specific embodiments illustrate various aspects of the invention. These examples should be construed to encompass any and all variations that become evident as a result of the teaching provided herein.

The examples below established proof of concept of gene augmentation therapy in RDH12 knock out (RDH12−/−) mice and HEK293 cells. Expression of codon optimized cDNA in HEK293 cells was shown to be 20% higher than the wildtype gene. Proviral plasmid backbones with modifications are described, substantially as in WO2012/158,757, but with different stuffer sequence (derived from phage lambda). The RDH12 coding sequence is codon optimized, allowing for more efficient expression. In addition, we have included both native and codon optimized hRDH12 sequences in the plasmid design, and have shown efficacy results both in vitro and in vivo.

The proviral plasmids generate proof-of-concept data, safety and preclinical toxicity data and ultimately human clinical trials for RDH12 patients. The invention described herein involves novel optimized cDNAs of Retinal Dehydrogenase 12 (RDH12) that encode a functional RDH12 protein. In one embodiment, a codon optimized cDNA is designed for treating LCA13. Transgene cassettes are optimized by genetic engineering and because different sequences of nucleotides in a codon can encode the same amino acid, one can alter the nucleotide sequence, but still generate the same protein product. In other words, one can take advantage of multiple "synonymous" codons to generate the same protein product.

Additional experiments are also being carried out in induced pluripotent stem cells (iPCs) derived from RDH12 patients. These data strongly suggest clinical relevance and usefulness of the proviral plasmids packaged in AAV vectors as a method to treat RDH12 induced ocular conditions. In addition, in vitro models such as HEK293 and iPS cells are useful for testing the potency of the vectors.

Example 1: Codon Optimized RDH12 Sequence

The codon-optimized nucleic acid sequence encoding a functional RDH12 SEQ ID NO: 3 was generated by modifying a nature human RDH12 sequence to add a complete Kozak consensus at the 5' end embedded in a NotI and by adding WI and BamHI sites at the 3' end (restriction sites for cloning). A TGA stop codon was embedded in the MI site to facilitate optimal epitope tagging. This embodiment also avoids the use of certain restriction enzymes identified above.

The open reading frame (ORF) of codon optimized SEQ ID NO:3 differs from the native sequence by 22%, i.e., it shares only 78% identity with native hRDH12, as shown in FIGS. 1A-1B.

Example 2—Construction of RDH12-Expressing AAV

We generated adeno-associated virus proviral cis-plasmids containing the human native RDH12 cDNA with and without a myc tag based on the p618 backbone (see U.S. Pat. No. 9,249,425, incorporated by reference herein for the sequences employed in p618). In these proviral plasmids, the hRDH12 cDNA is driven by the constitutive CMV.CβA promoter (CBAe), i.e., pAAV.CMVe.native-hRDH12 and AAV.CBAe.h-native RDH12.myc.

As described in U.S. Pat. No. 9,249,425, the proviral plasmids also contain a 5' AAV ITR sequence, the ITR flanked upstream by restriction site 1 and downstream by restriction site 2; (b) a promoter flanked upstream by restriction site 2 and downstream by restriction site 3; (c) a polylinker sequence comprising restriction site 3, restriction site 4 and restriction site 5. In the embodiment described here, the transgene comprising a codon optimized nucleic acid sequence that encodes RDH12 is located between any two of the restriction sites 3, 4 and 5, without modification thereof, wherein the transgene is operatively linked to, and under the regulatory control of, the promoter; (d) a polyadenylation sequence flanked upstream by restriction site 4 or 5 and downstream by restriction site 6; and (e) a 3' AAV ITR sequence flanked upstream by restriction site 6 and downstream by restriction site 7. Each restriction site 1 through 7 occurs only once in the plasmid and is cleaved by a different enzyme that cannot cleave another restriction site in the plasmid. Restriction sites 1 through 7 are positioned to permit independent and repeated removal, replacement or substitution of one or more of element (a), (b), (c), (d) and (e) or the entire AAV genome (a) through (e) from the plasmid. Such a proviral plasmid further comprises a plasmid backbone comprising elements necessary for replication in bacterial cells, and a resistance gene. In another embodiment, the plasmid backbone comprises one or more of (a) 5' and 3' transcriptional terminator/insulator sequences that isolate transcription in the backbone from transcription in the modular recombinant AAV genome; or (b) a non-coding stuffer sequence that increases the backbone length and prevents reverse packaging of non-functional AAV genomes. These transgene cassettes are compatible with the cargo capacity of AAV vectors. The constructs were verified by restriction mapping and DNA sequencing analysis.

Figure 10A:
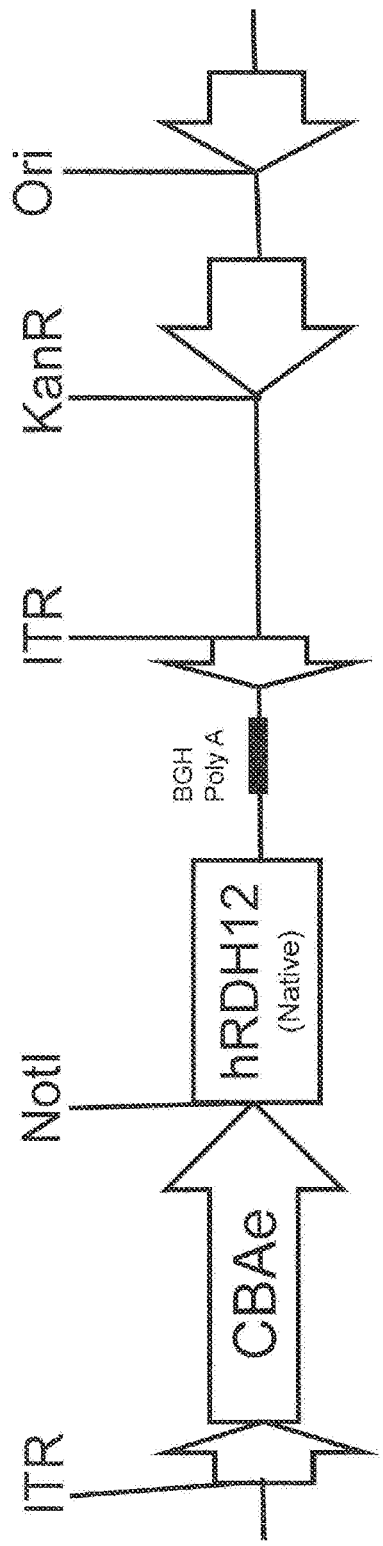
FIG. 10A is a schematic map of pAAV.CBAe.h-Native-RDH12, an expression cassette which contains between an AAV 5' ITR and 3'ITR, the native nucleic acid sequence encoding functional RDH12 under the control of regulatory sequences including the CMV.CβA promoter (CBAe), directing expression of the RDH12 in a selected cell.
Figure 10B:
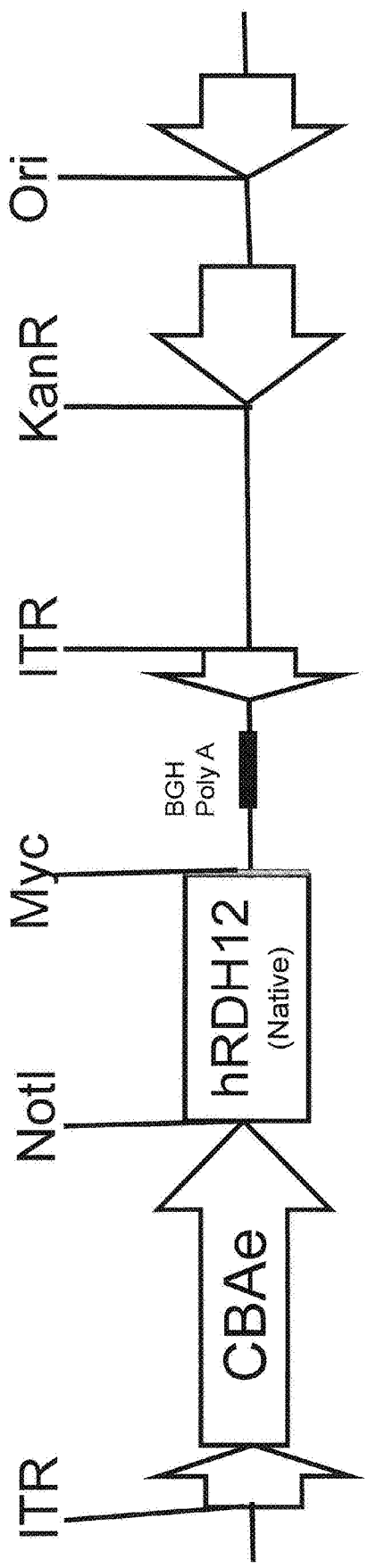
FIG. 10B is a schematic map of pAAV.CBAe.h-Native-RDH12.myc, an expression cassette which contains between an AAV 5' ITR and 3'ITR, the native nucleic acid sequence encoding functional RDH12 linked to a myc tag under the control of regulatory sequences including the CMV.CβA promoter directing expression of the RDH12 in a selected cell.
Figure 10C:
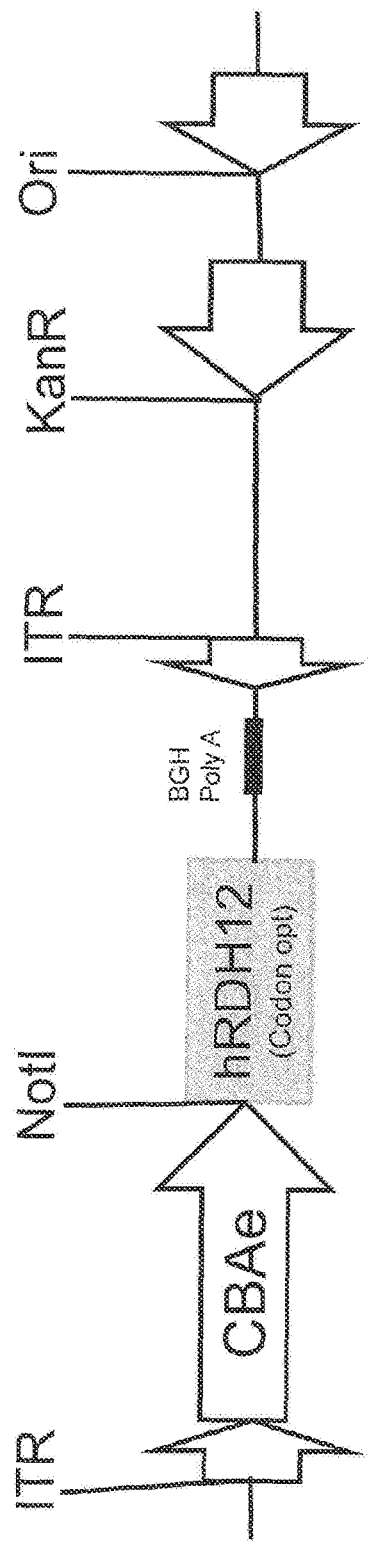
FIG. 10C is a schematic map of pAAV.CBAe.h-cocon opt-RDH12, an expression cassette which contains between an AAV 5' ITR and 3'ITR, the codon optimized nucleic acid sequence encoding functional RDH12 (SEQ ID NO: 3) linked to a myc tag under the control of regulatory sequences including the CMV.CβA promoter directing expression of the RDH12 in a selected cell.

See, e.g., the schematic drawings of AAV.CBAe.h-Native-RDH12, AAV.CBAe.h-Native RDH12-Myc and AAV.CBAe.h-codon opt-RDH12 of FIGS. 10A-10C, respectively.

To confirm the expression of the wild type (native) human RDH12 protein encoded in the proviral construct, COS-7 cells were transfected with pAAV-CMVe-native-hRDH12.myc. Transfected cells were subjected to immune fluorescence analysis and western blot analysis using antibodies specific to myc-tag.

Figure 2B:
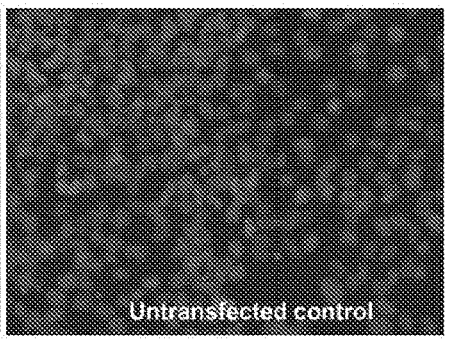
Figure 2C:
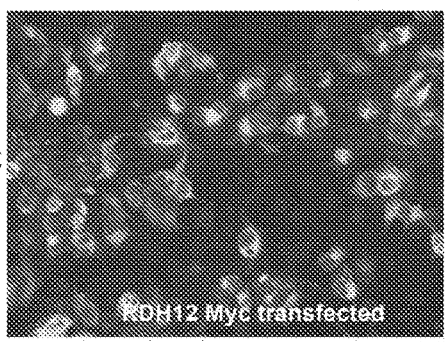
Figure 2D:
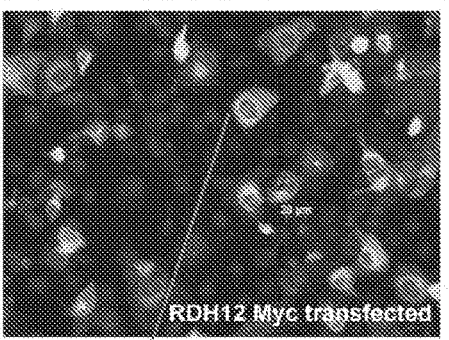
Figure 2E:
Figure 2F:
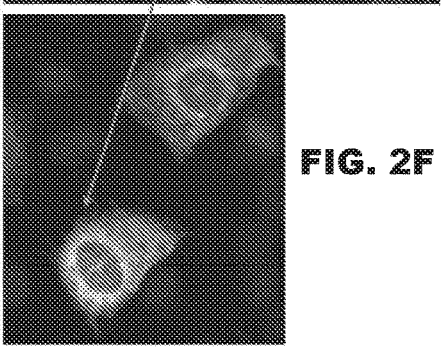

The cells were then stained and examined electroscopically to show successful transfection and the efficacy of gene transfer. Immunofluorescence analysis of cells transfected with pAAV.CMVe.native-hRDH12.myc demonstrated the expression of RDH12 protein in transfected cells only. FIGS. 2A-2F shows 6 panels indicating the expression of the RDH12 in the cells. FIGS. 2A-2B show untransfected control; FIGS. 2C-2D show RDH12Myc transfected cells; FIG. 2E shows RDH12Myc transfected cells; FIG. 2F is an enlargement of two cells from FIG. 2D.

Figure 2G:
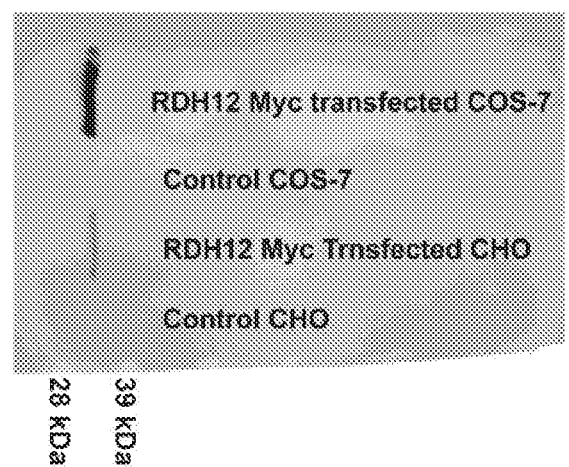
FIG. 2G is a gel showing RDH12Myc transfected COS-7 cells, control COS_7 cells, RDH12Myc transfected CHO cells and control Cho cells and two molecular weight markers.

Western blot analysis further confirmed the expression of expected size human RDH12 protein in transfected cells, with no band observed in control, untransfected cells. FIG. 2G is a gel showing RDH12Myc transfected COS-7 cells, control COS-7 cells, RDH12Myc transfected CHO cells and control CHO cells and two molecular weight markers. (FIG. 2G).

The pAAV.CMVe.native-hRDH12 and pAAV.CMVe.native-hRDH12.myc proviral plasmids were then used to produce recombinant AAV serotype vectors (AAV2, AAV8 and AAV7m8) using the triple transfection method involving transfection of subconfluent HEK293 cells by three plasmids: AAV cis-plasmid encoding the gene of interest, AAV trans-plasmid containing AAV rep and cap genes, and adenovirus helper plasmid, thereby generating AAV8-RDH12, AAV2-RDH12 and AAV7m8-RDH12.

Briefly described, the AAV8-RDH12-myc or AAV7m8-RDH12-myc expression cassettes are individually packaged in a selected AAV capsid by culturing a packaging cell carrying the plasmid in the presence of sufficient viral sequences to permit packaging of the AAV genome into an infectious AAV envelope or capsid. In one embodiment, a method for producing the rAAV involves packaging in a stable rep and cap expressing mammalian host packaging cell line (such as B-50 as described in International Patent Application Publication No. WO 99/15685) with the adenovirus E1, E2a, and E4ORF6 DNA. Iodixanol gradient purification or gradient centrifugation is used to separate DNA containing viral particles from the empty ones. This is followed by herparin-sepharose agarose column chromatography. Vector titers are determined using an infectious center assay. The vector genome is determined by silver staining against an established reference lot. The purity of the vectors is again examined by the clarity of a western gel. Virus preparations are prepared in and combined to a desired total volume.

Still other methods of producing such rAAV particles involve use of an insect cell packaging cell line, such as described in Smith et al, ref 11, cited below.

The rAAV viral particles are suspended in a suitable excipient, such as 180 mM NaCl, 10 mM NaPi, pH7.3, containing 0.0001%-0.01% Pluronic F68 (PF68). The composition of the saline component ranges from 160 mM to 180 mM NaCl. Other buffers are useful in such compositions, including HEPEs, sodium bicarbonate, TRIS, or 0.9% NaCl solution.

Several preparations of the rAAV are combined to a desired total volume. In one embodiment, a total volume is a dosage of $1 \times 10^{11}$ GC in a volume of 300 microliters of buffer. In another embodiment, a total volume is a dosage of $1 \times 10^{8}$ GC in a volume of 300 microliters of buffer. In still another embodiment, a total volume is a dosage of $1 \times 10^{6}$ to $1 \times 10^{13}$ GC in a volume of 300 microliters of buffer. Contaminating helper adenovirus and native AAV, assayed by serial dilution cytopathic effect or infectious center assay, respectively are anticipated to be less than one or multiples orders of magnitude lower than vector AAV.

Example 3—iPSCs as a Model System

Figure 4:
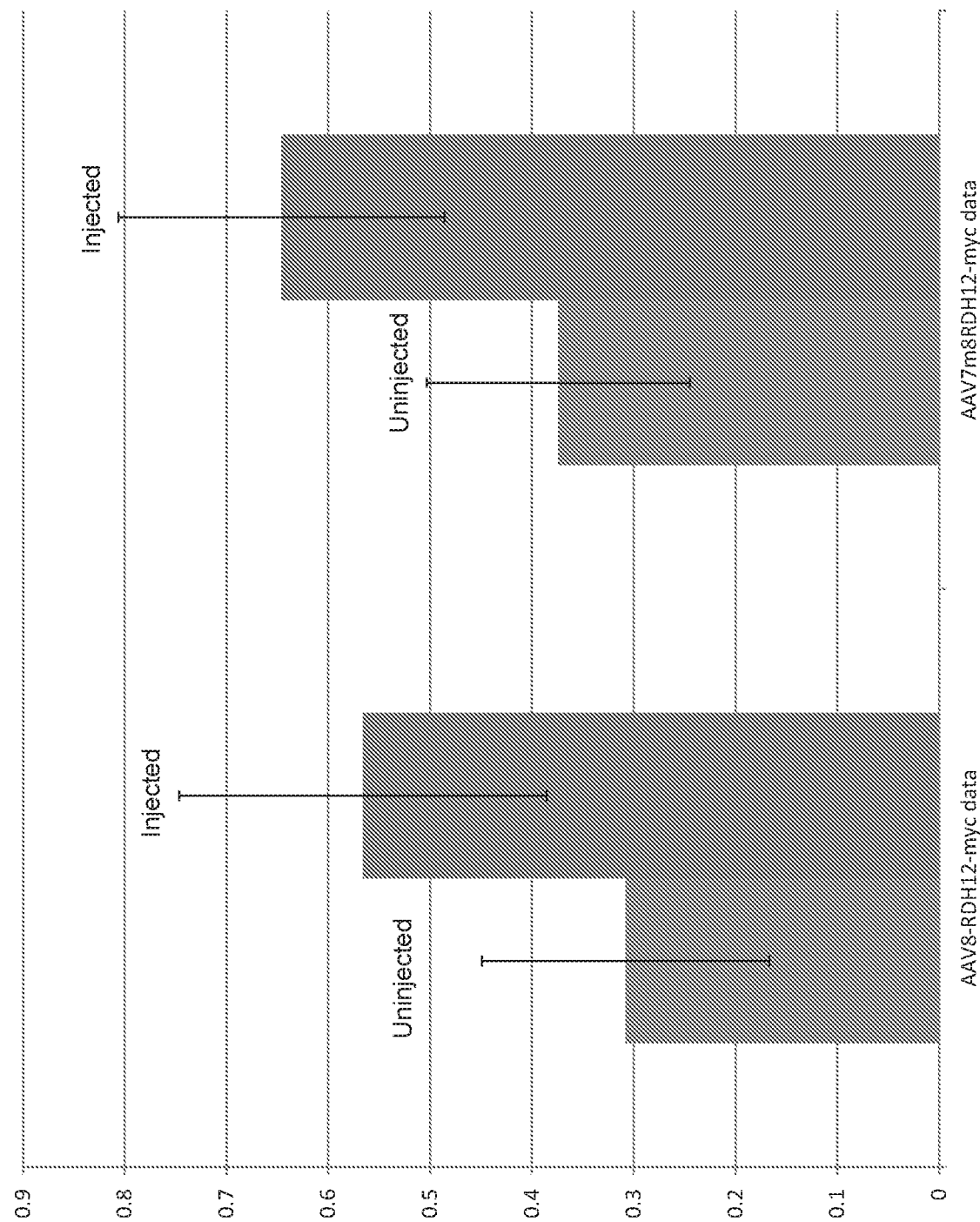
FIG. 4 is a graph showing A-wave prebleach and post bleach ratio in RDH12.myc injected vs. uninjected retinal of RDH12 KO mice with AAV8-RDH12-myc and AAV7m8RDH12-myc. Electroretinograms (ERG) were performed on RDH12−/− mice that were injected in one eye with our test vector. Contralateral uninjected eye was used as a control to compare the protective effect of exogenous RDh12 over light induced retinal damage. ERG were performed before and after light damage to compare the affect. Post light damage, Uninjected eyes showed a decrease in A-wave amplitudes, while the injected eyes remained relatively stable after light damage.

Recent advances in patient-specific induced pluripotent stem cells (iPSCs) provide a suitable in vitro model system to study disease pathogenesis. In order develop an in vitro model to study the function of RDH12, iPS cells were generated from a human RDH12 patient and characterized. To confirm that infection with AAV2.CMV.CβA-native-hRDH12 would result in the production of exogenous RDH12, we transduced aliquots of iPS cells with AAV2 CMV.CβA-native-hRDH12, with $1 \times 10^3$, $1 \times 10^4$, $1 \times 10^5$ or $2 \times 10^5$, $3 \times 10^5$ vector genomes (vg)/cell. Forty-eight hours later, cell lysates were collected and analyzed via western blotting using antibodies specific to myc tag. A clear dose-dependent production of human RDH12 was observed in the transduced cell lysates. See the results in FIG. 4.

Figure 3:
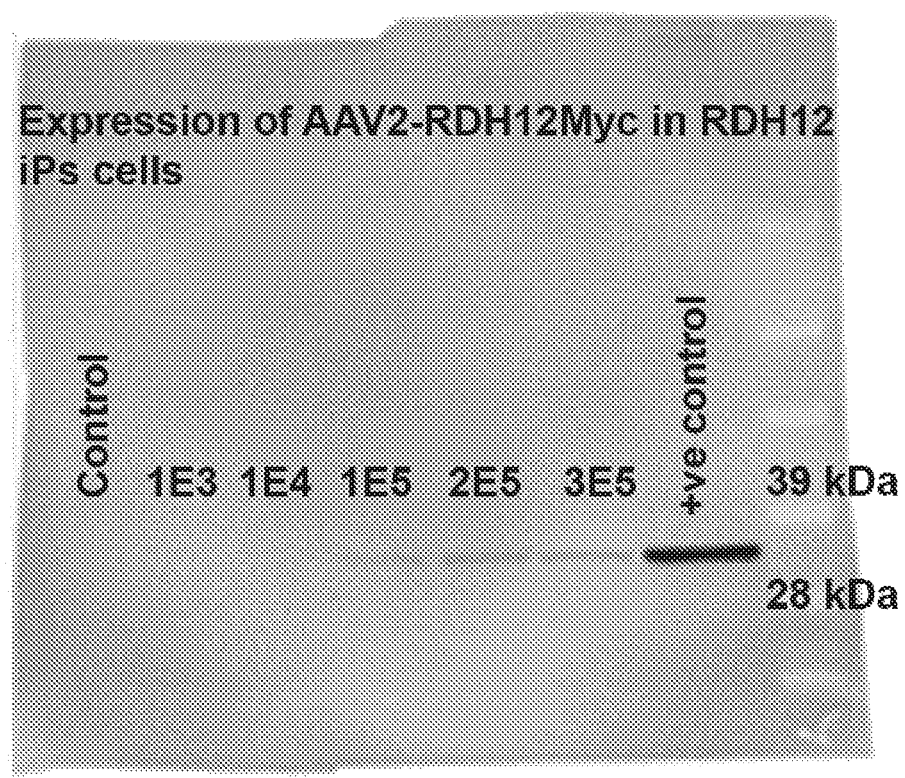
FIG. 3 is a gel showing expression of AAV2-RDH12Myc in RDH12 iPs cells. The cells are labeled and MW markers shown.

In another in vitro experiment, recombinant virus AAV2-RDH12-Myc was then transfected into iPS cells at the indicated multiplicity of transfection $1 \times 10^3$ GC/cell, $1 \times 10^4$ GC/cell, $1 \times 10^5$ GC/cell, $2 \times 10^5$ GC/cell, and $3 \times 10^5$ GC/cell. A positive control is also shown. Expression is confirmed as shown in FIG. 3.

Example 4—Light Damage of RDH12 KO Animals

Rdh12$^{-/-}$ mice with BALB/c background were obtained from Dr. Anne Kasus-Jacobi, University of Oklahoma. These animals do not exhibit a human retinal degeneration phenotype when raised under normal cyclic light, but undergo degeneration after exposure to bright light.

To evaluate the efficacy of gene augmentation therapy in RDH12$^{-/-}$ mice, the mice were pre-treated unilaterally with the experimental rAAVs (AAV8.CMV.CβA-native-hRDH12 or AAV7m8.CMV.CβA-native-hRDH12) and determined whether delivery of RDH12 protects these diseased retinas from light-induced degeneration. Animals at the age of 1-2 months were injected subretinally with AAV8.CMV.CβA-native-hRDH12 or intravitreally with AAV7m8.CMV.CβA-native-hRDH12 unilaterally. Each rAAV was injected in the right eye of a RDH12 KO mouse by injection of $10^{11}$-$10^{13}$ viral particles or $10^{11}$-$10^{13}$ viral particles/ml buffer with the left eye left uninfected. 3-4 weeks post injection, animals were exposed to a bright light (10,000 Lux) for 4 h.

Effect of light in the retinas of these animals were evaluated by retinal function studies (electroretinograms, (ERGs)) before and 24 h after light damage. Retina exposed to light should demonstrate evidence of light damage. Animals at that point were subjected to 10 day recovery period from light damage. We then measured the retinal function by ERG and the extent of photoreceptor cell death in retinal tissue sections. The mice were sacrificed and the eyes collected eyes for cryosectioning. Cryosectioned tissue is stained with Anti-myc antibody. Myc was non-specific. Nuclei were stained with DAPI.

Figure 5A:
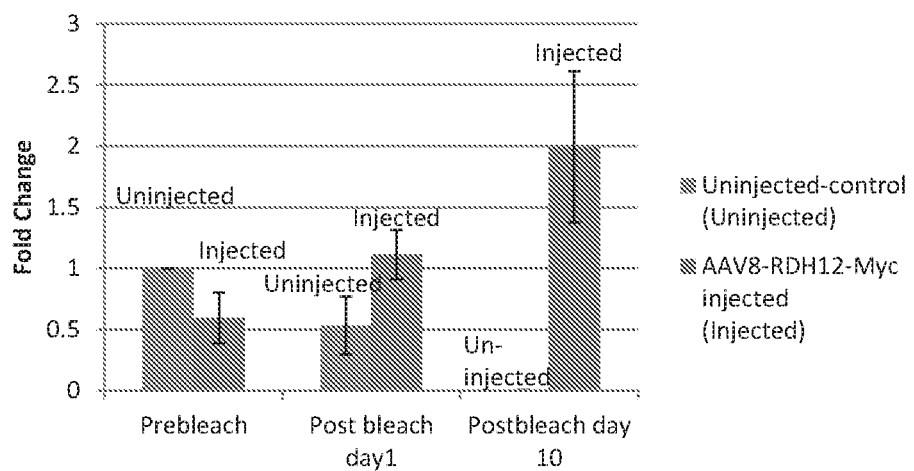
FIG. 5A shows a graph of an A-wave prebleach and post-bleach ratio in RDH12.myc (AAV8-RDH12-Myc) injected vs. uninjected retina of RDH12 KO mice.
Figure 5B:
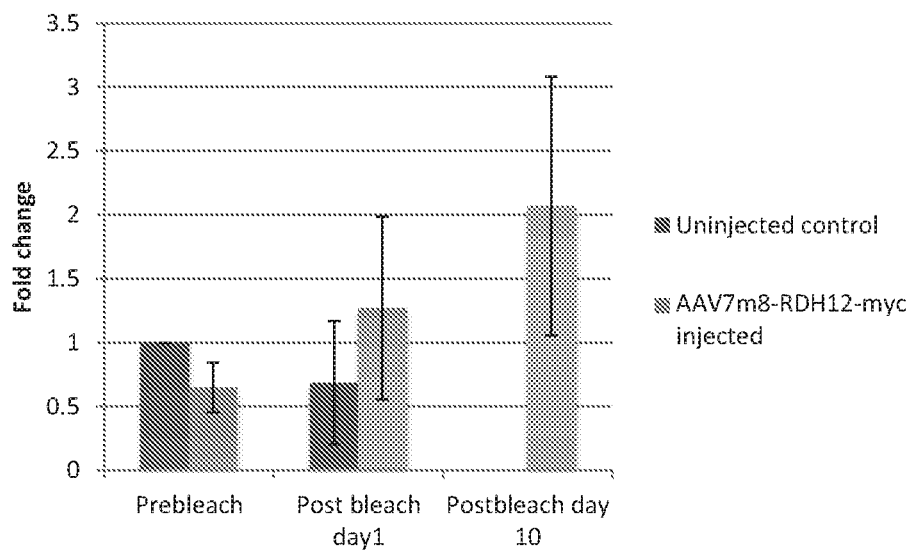
FIG. 5B shows a graph of an A-wave prebleach and post-bleach ratio in RDH12.myc (AAV7m8-RDH12-Myc) injected vs. uninjected retina of RDH12 KO mice.

FIGS. 5A and 5B show the a-wave amplitude differences in retinas of RDH12$^{-/-}$ mice injected either with AAV8 or AAV7m8. CMV.CβA-native-hRDH12 (AAV-RDH12) and untreated eyes. Electroretinography (ERG) revealed a partial functional rescue of the a-wave, which represents rod photoreceptor function, in AAV-RDH12 treated retinas after light exposure. FIG. 5A shows a graph of an A-wave ratio in RDH12.myc (AAV8-RDH12-Myc) injected vs. uninjected retina of RDH12 KO mice (prebleach and post-bleach). FIG. 5B shows a graph of an A-wave prebleach and post-bleach ratio in RDH12.myc (AAV7m8-RDH12-Myc) injected vs. uninjected retina of RDH12 KO mice.

Vector-treated RDH12$^{-/-}$ eyes were assessed for the degree of histological rescue that accompanied preservation of photoreceptor function after light damage (See FIGS. 6-9).

FIGS. 6A-6D shows experimental results for a single animal 136 in which the left eye (FIGS. 6A AND 6C) was uninjected. The right eye (FIGS. 6B and 6D) was injected with AAV7m8-RDH12-Myc. ERG baseline was performed followed by light damage, followed by a second ERG. The animals were housed for 10 days and a third ERG was performed. Mice were sacrificed and eyes collected fixed and sectioned and stained with DAPI ((FIGS. 6A and 6B)) or with rhodopsin and DAPI ((FIGS. 6C and 6D)).

Figure 7A:
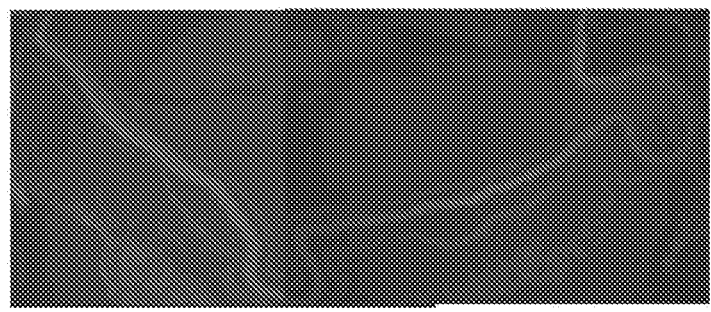
FIG. 7A through 7C show that retinal architecture is preserved in an AAV7m8-RDH12-Myc injected retina compared to uninjected retina after light damage.
Figure 7B:
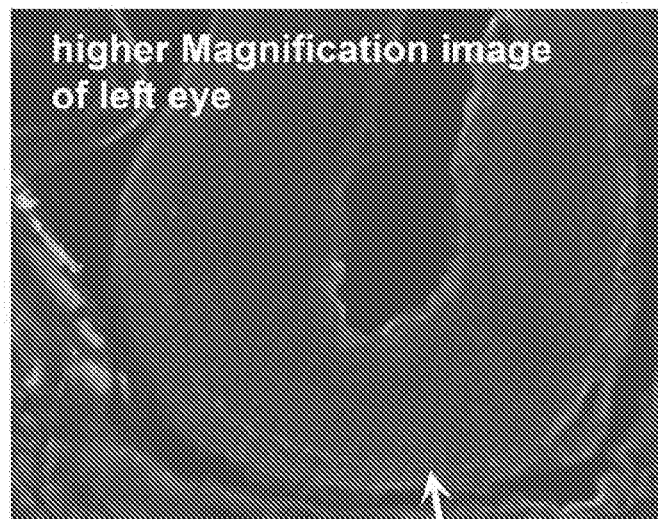
Figure 7C:
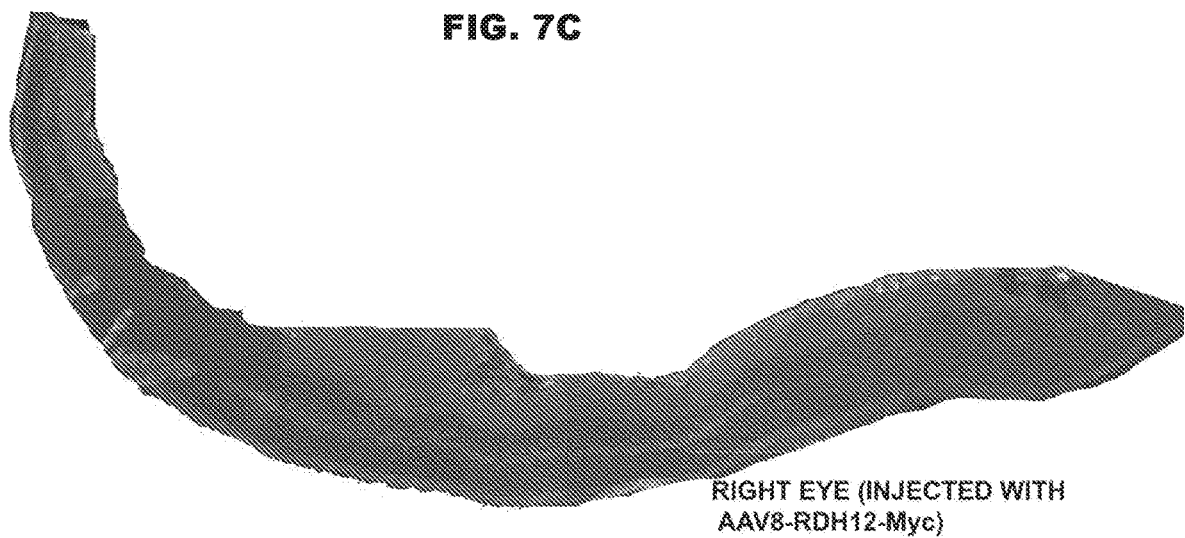

FIG. 7A through 7C shows that the retinal architecture is preserved in an AAV7m8-RDH12-Myc injected retina compared to uninjected retina after light damage. FIG. 7A shows the left uninjected eye. FIG. 7B shows a higher magnification image of the left eye, showing a thin ONL. FIG. 7C is a right eye injected with AAV7m8-RDH12-Myc.

FIG. 8A shows the retinal architecture of an animal with a left eye uninjected showing a thin retina. FIG. 8B shows the animal's right eye, injected with AAV8-RDH12-Myc.

FIGS. 9A and 9B show the retinal architecture of a single animal 147 with higher magnification images. FIG. 9A shows uninjected left eye. FIG. 9B shows right eye injected with AAV8-RDH12-Myc.

At low magnification, it is apparent that most treated RDH12$^{-/-}$ retinas maintained a relatively normal ONL, whereas in the untreated eye of the same mouse, the ONL contained few photoreceptor cell bodies in the central retinal region. Higher magnification images showed that a typical treated retina retained a substantial Outer nuclear thickness and outer segments. In contrast, in untreated eye from the same mouse, only one to three rows of ONL nuclei remained, with residual outer segments in the central retina.

The same tests are performed to confirm that the optimization of codon usage within the RDH12 gene results in increased levels of transgene expression and a better rescue of retinal degeneration. Codon optimization is anticipated to reduce the viral dose needed for effective reconstitution of RDH12.

Example 5—Efficacy in Human Subjects

The rAAV particles are also employed to transduce cells of human subject's retina after administration by subretinal injection of $10^{10}$-$10^{12}$ GC or viral particles in a suspension in a suitable buffered carrier. Expression of codon optimized hRDH12 in transduced cells or retinas is assessed by retinal and visual function.

These functions are examined in humans using one or more of the techniques: electroretinograms (ERGs) looking at rod and cone photoreceptor function pupillometry visual acuity contrast sensitivity color vision testing visual field testing (Humphrey visual fields/Goldmann visual fields) perimetry mobility test (obstacle course) reading speed test. Other useful tests include functional magnetic resonance imaging (fMRI) full-field light sensitivity testing, retinal structure studies including optical coherence tomography, fundus photography, fundus autofluorescence, adaptive optics and scanning laser ophthalmoscopy.

TABLE 1

| (Sequence Listing Free Text) The following information is provided for sequences containing free text under numeric identifier <223>. | |
|---|---|
| SEQ ID NO: (containing free text) | Free Text Under <223> |
| 3 | Codon optimized RDH12 DNA sequence |
| 4 | Translated functional RDH12 protein sequence from codon optimized nucleic acid sequence |

Each and every patent, patent application, including parent application U.S. 62/359,777 filed Jul. 8, 2016, and publication, are incorporated herein by reference. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A nucleic acid comprising a nucleotide sequence of SEQ ID NO: 5 encoding human RDH12.

2. An expression cassette comprising a nucleotide sequence of SEQ ID NO: 5 encoding human RDH12.

3. The expression cassette of claim 2, wherein said nucleotide sequence is operatively associated with expression control sequences that can direct expression of the nucleotide sequence in a host cell.

4. The expression cassette of claim 2, which is a recombinant adeno-associated virus (AAV) expression cassette further comprising a 5' AAV inverted terminal repeat (ITR) and a 3' AAV ITR, and expression control sequences that can direct expression of the nucleotide sequence in a host cell.

5. The rAAV expression cassette of claim 4, wherein the expression control sequences comprise a rhodopsin kinase promoter.

6. A vector or plasmid comprising the expression cassette of claim 2.

7. A vector or plasmid comprising the expression cassette of claim 4.

8. A recombinant adeno-associated virus (AAV) comprising an AAV capsid protein and a nucleotide sequence comprising a sequence set forth in SEQ ID NO: 5 encoding human RDH12 under the control of regulatory sequences which can express the human RDH12 in the photoreceptor cells of a subject.

9. The rAAV according to claim 8, wherein the rAAV comprises an AAV8 capsid, or variant thereof, an AAV7 capsid, or variant thereof, an AAV5 capsid, or variant thereof, or an AAV2 capsid, or variant thereof.

10. The rAAV according to claim 8, wherein the rAAV is a self-complementary AAV.

11. A host cell comprising the expression cassette of claim 2.

12. A composition comprising a nucleic acid molecule comprising a nucleotide sequence set forth in SEQ ID NO: 5 encoding human RDH12 under the control of regulatory sequences which can direct expression thereof in ocular cells; and a carrier or excipient suitable for delivery to the ocular cells of a subject.

13. The composition of claim 12, further comprising a recombinant virus comprising an AAV capsid protein and said nucleotide sequence.

14. The nucleic acid of claim 1, wherein the nucleotide sequence comprises nucleotides 1 to 949 of SEQ ID NO: 5.

15. The expression cassette according to claim 2, wherein the nucleotide sequence comprises nucleotides 1 to 949 of SEQ ID NO: 5.

16. The rAAV according to claim 8, wherein the nucleotide sequence comprises nucleotides 1 to 949 of SEQ ID NO: 5.

17. A rAAV comprising an AAV8 capsid and an expression cassette comprising:
   a) a 5' AAV ITR;
   b) a rhodopsin kinase promoter;
   c) the nucleotide sequence set forth in SEQ ID NO: 5; and
   d) a 3' AAV ITR.

\* \* \* \* \*